(12) United States Patent
Sewell et al.

(10) Patent No.: US 11,850,264 B2
(45) Date of Patent: Dec. 26, 2023

(54) GAMMA DELTA T-CELL RECEPTOR AND ITS LIGAND

(71) Applicant: University College Cardiff Consultants Ltd., Cardiff South Glamorgan (GB)

(72) Inventors: Andrew Sewell, Cardiff South Glamorgan (GB); Garry Dolton, Cardiff South Glamorgan (GB)

(73) Assignee: University College Cardiff Consultants Ltd., Cardiff South Wales (GB)

( * ) Notice: Subject to any disclaimer, the term of this patent is extended or adjusted under 35 U.S.C. 154(b) by 760 days.

(21) Appl. No.: 16/877,928

(22) Filed: May 19, 2020

(65) Prior Publication Data
US 2020/0316124 A1 Oct. 8, 2020

Related U.S. Application Data

(63) Continuation-in-part of application No. PCT/GB2018/053321, filed on Nov. 16, 2018.

(30) Foreign Application Priority Data

Nov. 20, 2017 (GB) .................................... 1719169

(51) Int. Cl.
| | |
|---|---|
| *A61K 35/17* | (2015.01) |
| *C07K 14/725* | (2006.01) |
| *C12N 7/00* | (2006.01) |
| *C12N 15/10* | (2006.01) |
| *C12N 15/86* | (2006.01) |
| *C07K 14/47* | (2006.01) |
| *A61P 35/00* | (2006.01) |
| *A61K 45/06* | (2006.01) |

(52) U.S. Cl.
CPC .............. *A61K 35/17* (2013.01); *A61P 35/00* (2018.01); *C07K 14/4748* (2013.01); *C07K 14/7051* (2013.01); *C12N 7/00* (2013.01); *C12N 15/1037* (2013.01); *C12N 15/86* (2013.01); *A61K 45/06* (2013.01); *C12N 2740/15043* (2013.01)

(58) Field of Classification Search
CPC ........ A61K 35/17; A61K 45/06; A61K 38/00; A61P 35/00; C07K 14/4748; C07K 14/7051; C12N 7/00; C12N 15/1037; C12N 15/86; C12N 2740/15043
See application file for complete search history.

(56) References Cited

U.S. PATENT DOCUMENTS

| | | | |
|---|---|---|---|
| 5,260,223 A | 11/1993 | Brenner et al. | |
| 2002/0142389 A1 | 10/2002 | Jakobsen et al. | |
| 2004/0072254 A1 | 4/2004 | Callamaras et al. | |
| 2017/0260271 A1 | 9/2017 | Igawa et al. | |

FOREIGN PATENT DOCUMENTS

| | | |
|---|---|---|
| EA | 201692287 A1 | 6/2017 |
| WO | 1996013593 A2 | 5/1996 |
| WO | WO 03/050262   * | 6/2003 |
| WO | 2005014848 A2 | 2/2005 |
| WO | 2013155406 A1 | 10/2013 |
| WO | 2015121454 A1 | 8/2015 |
| WO | 2015140268 A1 | 9/2015 |
| WO | 2016016344 A1 | 2/2016 |
| WO | 2016146618 A1 | 9/2016 |

OTHER PUBLICATIONS

Database UniProt [Online] (Oct. 1, 1994) "RecName: Full=Amiloride-sensitive sodium channel subunit alpha" RefSeq:XP002787613.1; XP002787613; Retrieved from EBI accession No. UNIPROT:P37088; DATAbase Accession No. P37088.
Braza et al. "Anti-tumour immunotherapy with V gamma9 V delta2 lymphocytes: from bench to the bedside", 2012, British Journal of Haematology, vol. 160, No. 2, 123-132.
Chen et al. "Deletion of ?-subunit exon 11 of the epithelial Na+ channel reveals a regulatory module.", Am J Physiol. Renal Physiol, 2014, vol. 306, No. 5, F561-7.
Donia et al. "PD-1 + polyfunctional T cells dominate the periphery after tumor-infiltrating lymphocyte therapy for cancer", Clin. Cancer Res., 2017, vol. 23, No. 19, 5779-5788.
Ekeruche-Makinde et al. "T-cell receptor-optimized peptide skewing of the T-cell repertoire can enhance antigen targeting", J. Biol. Chem., 2012, vol. 287, No. 44, 37269-37281.
Haney et al. "Isolation of viable antigen-specific CD8+ T cells based on membrane-bound tumor necrosis factor (TNF)-alpha expression", J. Immunol. Methods, 2011, vol. 369, No. 1-2, 33-41.
International Search Report for International Application No. PCT/GB2018/053321, dated Jan. 30, 2019 (5 pages).
Legut et al. "CRISPR-mediated TCR replacement generates superior anticancer transgenic T-cells", Blood, 2018, vol. 131, No. 3, 311-322 (Published as EPUB ahead of print, 2017).

(Continued)

*Primary Examiner* — Nelson B Moseley, II
(74) *Attorney, Agent, or Firm* — Dechert LLP; Andrew T. Wilkins; Sharla F. Flohr

(57) ABSTRACT

The present disclosure relates to a new T-cell receptor (TCR), in particular at least one complementarity-determining region (CDR) thereof; a T-cell expressing said TCR; a clone expressing said TCR; a vector encoding said TCR; a soluble version of said TCR; a pharmaceutical composition or immunogenic agent or bispecific or vaccine comprising said TCR, said cell, said clone or said vector; said TCR or said cell or said clone or said vector or said pharmaceutical composition or immunogenic agent or bispecific or vaccine for use in the treatment of cancer; a method of treating cancer using said TCR, said cell, said clone, said vector, said pharmaceutical composition, immunogenic agent, bispecific or vaccine comprising said TCR; and a ligand with which said TCR binds.

20 Claims, 11 Drawing Sheets

Specification includes a Sequence Listing.

(56) References Cited

OTHER PUBLICATIONS

Legut et al. "The promise of gamma delta T cells and the gamma delta T cell receptor for cancer immunotherapy", Cellular & Molecular Immunology, 2015, vol. 12, No. 6, 656-668.
Patel et al. "Identification of essential genes for cancer immunotherapy", Nature, 2017, vol. 548, 537-542.
Simões et al. "Molecular Determinants of Target Cell Recognition by Human gamma delta T Cells", 2018, Frontiers in Immunology, vol. 9, 929.
Theaker et al. "T-cell libraries allow simple parallel generation of multiple peptide-specific human T-cell clones", J. Immunol. Methods, 2016, vol. 430, 43-50.
Liang et al., "Recombination-based DNA assembly and mutagenesis methods for metabolic engineering," Methods Mol Biol., 843: 93-109 (2012).
"Beta ENaC Polyclonal antibody", Proteintech (2013).
Cohen et al., "Enhanced antitumor activity of murine-human hybrid T-cell receptor (TCR) in human lymphocytes is associated with improved pairing and TCR/CD3 stability," Cancer Res. 2006 66(17): 8878-86 doi: 10.1158/0008-5472.CAN-06-1450.
Gründer et al., "Gamma-9 and delta-2CDR3 domains regulate functional avidity of T cells harboring gamma-9-delta-2TCRs," Blood 2012 120(26): 5153-62 doi: 10.1182/blood-2012-05-432427. Epub Sep. 27, 2012.

\* cited by examiner

Fig. 3A
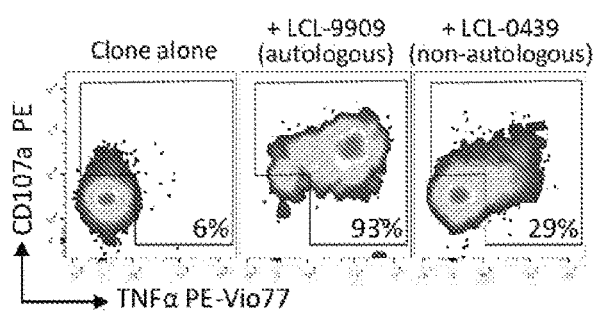
Fig. 3C
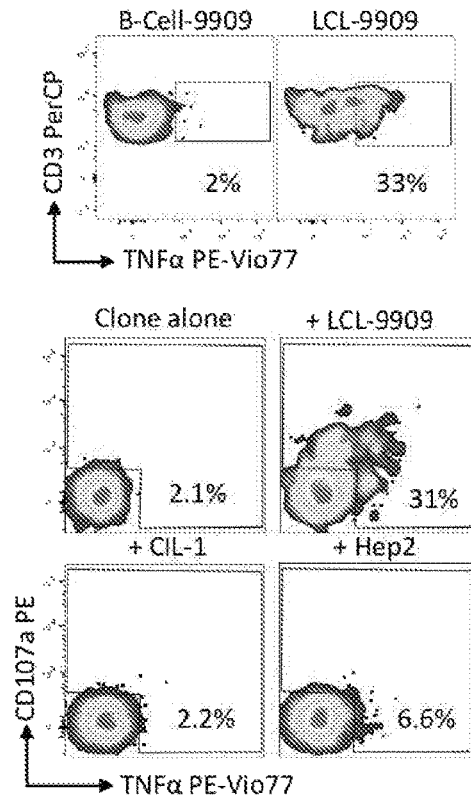
Fig. 3B
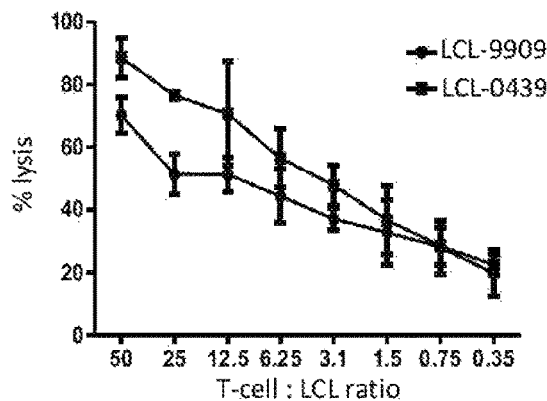
Fig. 3D

Fig. 7A

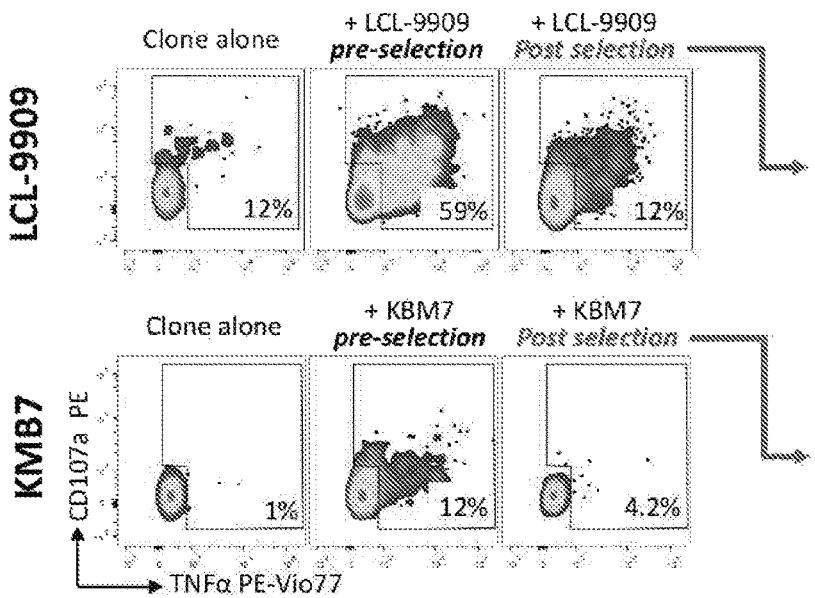

Fig. 7B

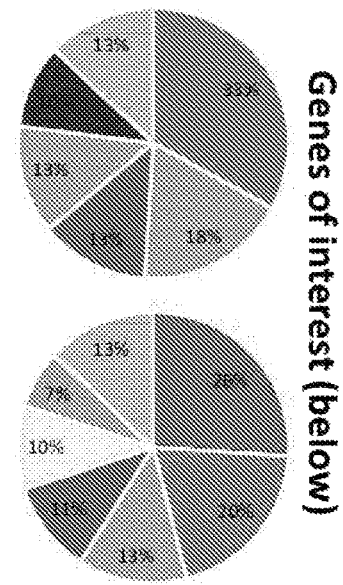

Genes of interest (below)

Fig. 7C

LCL-9909 and KMB7:

Gene: SCNN1A (Sodium Channel Epithelial 1 Alpha Subunit)
http://www.uniprot.org/uniprot/P37088

Gene: DTNB (Dystrobrevin Beta)
http://www.uniprot.org/uniprot/Q60941

Gene: NDUFV3 (NADH: Ubiquinone Oxidoreductase Subunit V3)
http://www.uniprot.org/uniprot/P56181

Gene: LRRIQ3 (Leucine Rich Repeats and IQ Motif Containing 3)
http://www.uniprot.org/uniprot/A6PVS8

Other genes

LCL-9909:

Gene: Homo sapiens (Hsa) MIR610 (microRNA 610)
http://www.genecards.org/cgi-bin/carddisp.pl?gene=MIR610

KBM7:

Gene: ZYX (Zyxin)
http://www.uniprot.org/uniprot/Q15942

Gene: NSUN5 (Probable 28S rRNA (cytosine-C(5))-methyltransferase)
http://www.uniprot.org/uniprot/Q96P11

Gene Aliases: SCNN1A; BESC2; ENaCa; ENaCalpha; SCNEA; SCNN1.

Protein Aliases: alpha ENaC-2; Alpha-ENaC; Alpha-NaCH; amiloride-sensitive epithelial sodium channel alpha subunit; Amiloride-sensitive sodium channel subunit alpha; amiloride-sensitive sodium channel subunit alpha 2; ENaCalpha; Epithelial a (+) channel subunit alpha; Epithelial Na(+) channel subunit alpha; FLJ21883; nasal epithelial sodium channel alpha subunit; Nonvoltage-gated sodium channel 1 subunit alpha; SCNEA; SCNN1; sodium channel, non voltage gated 1 alpha subunit; sodium channel, non-voltage-gated 1 alpha subunit; sodium channel, nonvoltage-gated 1 alpha.

Isoforms: Six splice variant isoforms described (Figure 9). Universal Protein Source (UniProt) identification: P37088-1, -2, -3, -4, -5 and -6. Isoform 1 is considered the canonical sequence and was *used for this study*. Amino acid length and size (kDa) for each respective isoform: 669/75,704; 728/81.856; 245/28,328; 650/73,603; 691/77,980; 692/78,234. Natural variants have been described.

Antibodies: *PA5-29136*: Rabbit polyclonal anti-human against residues 272-555. *PA5-35364*: Rabbit polyclonal against residues 365-391. *PA1-920A*: Rabbit polyclonal anti-human (crossreacts with mouse and rat) against residues 20-42, and was *used for this study*. *OSR00124W*: Rabbit polyclonal anti-human against the extracellular domain.

Homology with other species: 90% with other primates and 50% with mouse.

GAMMA DELTA T-CELL RECEPTOR AND ITS LIGAND

CROSS REFERENCE

This is a Continuation-in-Part Application of PCT/GB2018/053321 filed Nov. 16, 2018, which claims priority to GB 1719169.3 filed Nov. 20, 2017, the contents of each of which are hereby incorporated by reference in their entirety.

SEQUENCE LISTING

The instant application contains a Sequence Listing in .txt format which has been submitted via EFS-Web and is herein incorporated by reference in its entirety. The Sequence Listing, created on Jul. 13, 2023 is named 2023-07-13 CFF-P2729USCIP Updated sequence listing.txt and is 37,772 bytes in size.

TECHNICAL FIELD

The present disclosure relates to a new T-cell receptor (TCR), in particular at least one complementarity-determining region (CDR) thereof; a T-cell expressing said TCR; a clone expressing said TCR; a vector encoding said TCR; a soluble version of said TCR; a pharmaceutical composition or immunogenic agent or bispecific or vaccine comprising said TCR, said cell, said clone or said vector; use of said TCR or said cell or said clone or said vector or said pharmaceutical composition or immunogenic agent or bispecific or vaccine to treat cancer; a method of treating cancer using said TCR, said cell, said clone, said vector, said pharmaceutical composition, immunogenic agent, bispecific or vaccine comprising said TCR; and a ligand with which said TCR binds.

BACKGROUND

We have discovered a new class of γδ T-cell effective for treating cancer, which require that the target cell expresses an intact SCNN1A gene for recognition. This T-cell does not follow the convention of requiring a specific Human Leukocyte Antigen (HLA) for target recognition and is therefore said to be 'unconventional'. The HLA locus is highly variable with over 17,000 different alleles having been described today. As such, any therapeutic approach that works via an HLA can only be effective in a minority of patients. In contrast, the entire human population expresses SCNN1A, the gene required for recognition of cancer cells via our γδ TCR and its corresponding new T-cell clone, termed hereinafter SW.3G1. This clone was discovered during a screen for γδ T-cells that could recognize Lymphoblastoid Cell Lines (LCLs) created by infecting healthy B-cells with Epstein-Barr virus (EBV) also called human herpesvirus 4 (HHV-4). Advantageously, the SW.3G1 γδ T-cell clone does not respond to healthy B-cells or other healthy cell lines.

Further studies have shown that the SW.3G1 γδ T-cell clone can recognize most, if not all, cancer cells. The SCNN1A gene is required for this recognition and so is the binding ligand for the SW.3G1 TCR.

As is known, and as shown in FIG. 2, the TCR is a disulfide-linked membrane-anchored heterodimeric protein normally consisting of the highly variable gamma and delta chains that associate with the invariant CD3 chain molecules to form a complete functioning TCR. T cells expressing this receptor are referred to as γ:δ (or γδ) T cells.

The γ and δ chains are composed of extracellular domains comprising a Constant (C) region and a Variable (V) region. The Constant region is proximal to the cell membrane, followed by a transmembrane region and a short cytoplasmic tail, while the Variable region binds to the ligand. The ligand for most γδ T cells remains unknown.

The variable domain of both the TCR γ-chain and δ-chain each has three variable regions called complementarity determining regions (CDRs). In general, the antigen-binding site is formed by the CDR loops of the TCR γ-chain and δ-chain. CDR1γ and CDR2γ are encoded by the individual Vγ genes whereas CDR1δ and CDR2δ are encoded by the individual Vδ genes. The CDR3 of the TCRγ-chain is hypervariable due to the potential for nucleotide addition and removal around the joining of the V region and a Joining region. The TCR δ-chain CDR3 has even more capacity for variation as it can also include a diversity (D) gene after VDJ recombination has occurred.

In 2015 about 90.5 million people had cancer. About 14.1 million new cases occur a year (not including skin cancer other than melanoma). It causes about 8.8 million deaths (15.7%) of human deaths. The most common types of cancer in males are lung cancer, prostate cancer, colorectal cancer and stomach cancer. In females, the most common types of cancer are breast cancer, colorectal cancer, lung cancer and cervical cancer. If skin cancer, other than melanoma, were included in total new cancers each year it would account for around 40% of cases. In children, acute lymphoblastic leukaemia and brain tumours are most common except in Africa where non-Hodgkin lymphoma occurs more often. In 2012, about 165,000 children under 15 years of age were diagnosed with cancer. The risk of cancer increases significantly with age and many cancers occur more commonly in developed countries. Rates are increasing as more people live to an old age and as lifestyle changes occur in the developing world. The financial costs of cancer were estimated at $1.16 trillion USD per year as of 2010. It follows that there is a need to provide better and safer ways of treating or eradicating this disease. An immunotherapy that uses the body's natural defence systems to kill aberrant tissue is acknowledged to be safer than chemical intervention but, to be effective, the immunotherapy must be cancer specific. Moreover, the discovery of an immunotherapy that is effective against any type of cancer would be extremely beneficial as not only could it be administered to individuals suffering from many different types of cancer (i.e. it would have pan-population application) but it could also be administered to a single individual suffering from more than one type of cancer. Additionally, the identification of an immunotherapy that was not MHC-restricted would also be extremely advantageous as it means it could be administered to any individual regardless of MHC tissue type.

The T-cells we have identified herein have the afore advantageous characteristics in that they are effective against any type of cancer and they are not MHC-restricted and so have pan-population application due to the ubiquitous expression of the SCNN1A gene product that is required for recognition.

STATEMENTS OF INVENTION

According to a first aspect of the invention there is provided a tumour specific T-cell receptor (TCR), or a fragment thereof, characterised by at least one complementarity-determining region (CDR) comprising or consisting of CATWDRRDYKKLF (SEQ ID NO: 1) and/or CAL-GVLPTVTGGGLIF (SEQ ID No: 2).

In a preferred embodiment of the invention said CDR comprises or consists of (CDR) CATWDRRDYKKLF (SEQ ID NO: 1) and/or CALGVLPTVTGGGLIF (SEQ ID No: 2) or a CDR that shares at least 88% identity therewith, such as 89%, 90%, 91%, 92%, 93%, 94%, 95%, 96%, 97%, 98% or 99%.

The CDRs described herein represent the CDR3s of said TCR and so are the main CDRs responsible for recognizing processed antigen or ligand. The other CDRs (CDR1gamma, CDR2gamma, CDR1delta and CDR2delta) are encoded by the germline. Therefore, the invention further concerns a TCR also including one or more of these other CDRs i.e. CDR1gamma, CDR2gamma, CDR1delta and/or CDR2delta in combination with the said one or more CDR3 sequences.

Accordingly, in a preferred embodiment said TCR comprises or consists of one or more, including any combination, of the following complementarity-determining regions:

```
                                    SEQ ID NO: 3
VTNTFY (CDR1γ)

SEQ ID NO: 4
YDVSTARD (CDR2γ)

SEQ ID NO: 5
TSWWSYY (CDR1δ)

SEQ ID NO: 6
QGS (CDR2δ)
```

Reference herein to a tumour specific TCR is to a TCR that specifically recognises a tumour cell or a tumour cell ligand, in the context of SCNN1A gene expression, and is activated by same but is not activated by a non-tumour cell or a non-tumour cell ligand.

In a preferred embodiment of the invention said TCR is an γδ TCR having a γ chain and a δ chain and said CDR of said γ chain comprises or consists of the CDR: CATWDRRDYKKLF (SEQ ID NO: 1) or a CDR that shares at least 88% identity therewith, such as 89%, 90%, 91%, 92%, 93%, 94%, 95%, 96%, 97%, 98% or 99%; and said CDR of said δ chain comprises or consists of the CDR: CALGVLPTVTGGGLIF (SEQ ID No: 2) or a CDR that shares at least 88% identity therewith, such as 89%, 90%, 91%, 92%, 93%, 94%, 95%, 96%, 97%, 98% or 99%. Accordingly, said TCR may comprise one or both of the afore CDRs and in a preferred embodiment comprises both of said CDRs.

In a further preferred embodiment of the invention said CDR of said TCR additionally or alternatively comprises or consists of a gamma chain sequence that is CALWEVDYKKLF (SEQ ID NO: 9) and/or a delta chain sequence that is CALGEPVLFAVRGLIF (SEQ ID NO: 10) and/or CACDLLGDRYTDKLIF (SEQ ID NO: 11) or a CDR that shares at least 88% identity therewith, such as 89%, 90%, 91%, 92%, 93%, 94%, 95%, 96%, 97%, 98% or 99%.

In yet a further preferred embodiment said TCR is unconventional in that it is not MHC-restricted, rather it binds to a tumour specific ligand in the context of SCNN1A gene expression. The fact that these T-cells and their TCRs are not MHC-restricted means they have pan-population therapy potential and so represent an extremely important new cancer therapy.

In a further preferred embodiment of the invention said TCR γ chain comprises or consists of:

```
                                       (SEQ ID NO: 7)
SSNLEGRTKSVTRQTGSSAEITCDLTVTNTFYIHWYLHQEGKAPQRLLY

YDVSTARDVLESGLSPGKYYTHTPRRWSWILRLQNLIENDSGVYYCATW

DRRDYKKLFGSGTTLVVTDKQLDADVSPKPTIFLPSIAETKLQKAGTYL

CLLEKFFPDVIKIHWQEKKSNTILGSQEGNTMKTNDTYMKFSWLTVPEK

SLDKEHRCIVRHENNKNGVDQEIIFPPIKT
``` or a sequence that has at least 88% identity therewith, such as 89%, 90%, 91%, 92%, 93%, 94%, 95%, 96%, 97%, 98% or 99%.

In a further preferred embodiment of the invention said TCR δ chain comprises or consists of:

```
                                       (SEQ ID NO: 8)
AQKVTQAQSSVSMPVRKAVTLNCLYETSWWSYYIFWYKQLPSKEMIFLI

RQGSDEQNAKSGRYSVNFKKAAKSVALTISALQLEDSAKYFCALGVLPT

VTGGGLIFGKGTRVTVEPNSQPHTKPSVFVMKNGTNVACLVKEFYPKDI

RINLVSSKKITEFDPAIVISPSGKYNAVKLGKYEDSNSVTCSVQHDNKT

VHSTDFEVKTDST
``` or a sequence that has at least 88% identity therewith, such as 89%, 90%, 91%, 92%, 93%, 94%, 95%, 96%, 97%, 98% or 99%.

(In the above paragraphs, the bold and underlined text represents the CDRs i.e. 1, 2, and 3 in that order).

In yet a further preferred embodiment of the invention said TCR comprises said afore TCR γ chain and said afore TCR δ chain.

In yet a further preferred embodiment, said TCR is a soluble TCR, or sTCR, and so lacks the transmembrane and, ideally also, intracellular domains.

In yet another preferred embodiment of the invention said TCR is part of a chimeric receptor having the functionality described herein. Ideally, said TCR is fused to an αβ TCR constant domain.

In the alternative, there is provided a fragment of said TCR such as a monomeric part thereof, ideally a single chain form of the TCR.

According to a further aspect of the invention there is provided a T-cell expressing said TCR of the invention, ideally, in either a soluble or membrane compatible form i.e. having a transmembrane region and intracellular region.

According to a yet further aspect of the invention there is provided a T-cell clone expressing said TCR of the invention, ideally, in either a soluble or membrane compatible form i.e. having a transmembrane region and intracellular region. Preferably said clone is a SW.3G1 clone as described herein.

According to a yet further aspect of the invention there is provided a vector encoding said TCR of the invention.

According to a yet further aspect of the invention there is provided a pharmaceutical composition or immunogenic agent or bispecific or vaccine comprising said TCR or cell or clone or vector of the invention.

In a preferred embodiment said pharmaceutical composition or immunogenic agent or bispecific or vaccine is used to treat any cancer, ideally colorectal cancer, lung, kidney, prostrate, bladder, cervical, melanoma (skin), bone, breast, blood cancer, brain, pancreas, testicle, ovary, head/neck, liver, bladder, thyroid, and uterine.

According to a yet further aspect of the invention there is provided the TCR or cell or clone or vector as herein described for use in the treatment of cancer.

According to a yet further aspect of the invention there is provided a method of treating cancer comprising administering said TCR or cell or clone or vector to an individual to be treated.

Ideally said cancer is of any type but in particular colorectal cancer, lung, kidney, prostrate, bladder, cervical, melanoma (skin), bone, breast, blood cancer, brain, pancreas, testicle, ovary, head/neck, liver, bladder, thyroid, and uterine.

In a preferred method of the invention said TCR, cell, clone or vector is administered in combination with an anti-tumour agent such as, but not limited to, a bispecific.

Reference herein to a bispecific is reference to a bispecific monoclonal antibody (BsMAb, BsAb) which is an artificial protein that can simultaneously bind to two different types of antigen.

Alternatively still, said TCR may form part of a Bispecific wherein said bispecific includes said TCR, for the purpose of binding to its ligand on a cancer cell, and also an immune cell activating component or ligand that binds and so activates an immune cell such as a Killer T-cell.

According to a yet further aspect of the invention there is provided the use of said TCR or cell or clone or vector in the manufacture of a medicament to treat cancer.

According to a yet further aspect of the invention there is provided a combination therapeutic for the treatment of cancer comprising:
 a) said TCR or cell or clone or vector or immunogenic agent or bispecific or vaccine in combination with
 b) a further cancer therapeutic agent.

According to a yet further aspect of the invention there is provided a TCR or polypeptide or bispecific or antibody, or a fragment of said antibody, that binds to at least one of the SCNNA1 gene product isoforms shown in FIG. 9 and in particular the extracellular domain thereof.

In a preferred embodiment of the invention said polypeptide, antibody or fragment inhibits the activity of said SCNNA1 gene product and, in the instance of said antibody is most ideally monoclonal.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

BRIEF DESCRIPTION OF THE DRAWINGS

An embodiment of the present invention will now be described by way of example only with reference to the following wherein:

FIG. 1A: Purified δδ T-cells from a healthy donor, 9909, were primed (day 0) and re-stimulated (day 14) with a pool of LCLs from three donors (0439, pt146 and Hom-2). On day 28 the T-cell line was incubated with the LCLs used for priming and also autologous LCL-9909 for 4 h with activation assessed by inclusion of TAPI-0, anti-CD107a and anti-TNFα antibodies. The activated cells were sorted by flow cytometry and the T-cell receptors (TCRs) analysed by next generation sequencing. Pie charts depict the proportion of the displayed TCR chains and CDR3s (complementarity determining regions) that were present in the sorted cells. The percentage of activated cells for the flow cytometry plots is shown above each gate. T-cell clone SW.3G1 obtained from the lines expresses the highlighted TCR chains, with the full TCR sequence shown in FIG. 2. FIG. 1B: Clone SW.3G1 was phenotyped with the antibodies and confirmed to express a TCRδ1 chain. SW.3G1 did not express an αβTCR or CD8 or CD4 glycoproteins associated with recognition of conventional peptide-HLA antigens.

FIGS. 3A-3D show SW.3G1 can recognize and kill autologous and non-autologous LCLs, but not healthy cells of various tissue origins. FIG. 3A: Co-incubation of SW.3G1 with LCLs for 4 h, with activation assessed by inclusion of TAPI-0, anti-CD107a and anti-TNFα antibodies. FIG. 3B: 6.5 h chromium release cytotoxicity assay using the same LCLs as in FIG. 3A. FIG. 3C: Autologous healthy B-cells magnetically purified directly ex-vivo from donor 9909 were used in activations assays as in FIG. 3A, with LCL-9909 used as a positive control for activation. FIG. 3D: Activation assays as in FIG. 3A, using LCL-9909 and the healthy cell lines, CIL-1 (non-pigmented ciliary epithelium) and Hep2 (hepatocyte). Percentage of gated cells is shown.

FIG. 4A: A panel of lymphoblastic cell lines (LCLs) from 24 donors (named on the x-axis). Red bars for LCLs that were used to generate the T-cell lines from donor 9909 from which SW.3G1 was cloned. T-cell to LCL ratio of 1:1. FIG. 4B: SW.3G1-mediated killing of panel of cancer cell lines (named on the x-axis) of different tissue origin (key) at a T-cell to cancer cell ratio of 10:1.

FIG. 5A: γδ SW.3G1 clone was co-incubated for 4 h with HMB-PP, the lymphoblastic cell line (LCL)-9909 and phytohaemagluttinin (PHA). T-cells were also incubated alone. T-cell activation was assessed by inclusion of TAPI-0, anti-CD107a and anti-TNFα antibodies, with the percentage of activated cells shown above the gated cells. FIG. 5B: Using the same activation assay as in FIG. 5A, SW.3G1 was incubated with LCLs that had been pre-labelled with antibodies (Abs) that bind the proteins named on the x-axis. SW.3G1 was also incubated with the LCLs without Ab (no Ab control). The percentage of reactivity is shown graphically (y-axis). MICA/B (Major Histocompatibility Complex (MHC) Class-I related chain A/B) and EPCR (Endothelial protein C receptor). Anti-MHC class I and II Abs were also included.

FIGS. 7A-7C show the results of the whole genome CRISPR/Cas9 approach that identified multiple candidate genes for target cell recognition by SW.3G1. FIG. 7A: Autologous LCL-9909 and cancer cell line KBM7s were transduced with a whole genome CRISPR/Cas9 library. The libraries were put though several selections using the SW.3G1 T-cell clone to generate a target cell line that was resistant to lysis. The surviving target cells (post-selection) were tested alongside the pre-selected cell lines in activation assays with SW.3G1. Activation assessed by inclusion of TAPI-0, anti-CD107a and anti-TNFα antibodies. FIG. 7B: Sequencing of the post-selection libraries revealed enriched guide RNAs corresponding to the genes shown in FIG. 7C. FIG. 7C: Candidate genes seen in both the LCL-9909 and KBM7 libraries, or seen only for LCL-9909 or KBM7s. Gene and (protein) names are shown with website links for further information.

FIG. 8 shows information about the candidate gene/protein SCNN1A, which was identified by the whole genome CRISPR/cas9 library approach.

FIG. 9 shows the canonical protein sequence of SCNN1A which aligned with five expressed splice variants. Isoform 1 is the canonical sequence (Isoform 1 UniProt P37088-1). Highlighted amino acids in BLACK: region used to generate the polyclonal Ab used in this study. RED: Sites of protein variants due to different amino acid residues to the ones shown. The amino acid residues of the protein variants and are not displayed here, but can be found at http://www.uniprot.org/uniprot/P37088. BLUE: amino acid differences between splice isoforms.

FIG. 10A: Schematic of the SCNN1A gene and protein, with guide RNA (gRNA) sites from the whole genome GeCKO library (number 1) and a different validation gRNA SCNN1A sequence we designed (number 2). Figure adapted from Chen 2014. FIG. 10B: Long term killing assay using SW.3G1 with LCL 0.174 wild-type, GeCKO gRNA-1 and gRNA-2 knock-out LCL.174 cells. FIG. 10C: Western blot analysis of the breast cancer cell line MDA-MB-231 that had received the gRNA-2 for SCNN1A. Wild-type cells used for comparison, with red arrow indicating the 76 kDa SCNN1A protein. FIG. 10D: MDA-MB-231 cells from FIG. 10C and melanoma MM909.24, wild-type and SCNN1A knock-out (KO) cell lines used in long term killing assays with SW.3G1. Cancer cells were used as lines and selected by puromycin treatment for those expressing the gRNAs, with no subsequent cell cloning.

FIG. 11A: Purified CD8+ T-cells from three donors were co-transduced with the SW.3G1 T-cell receptor chains (marker and purification via rat(r)CD2) and a gRNA to render the recipient T-cells TCRβ chain negative (selected by puromyicn treatment) (Legut et al 2017). Purity of the cells was checked with rCD2 antibody (Ab) and anti-γδ TCR Ab. FIG. 11B: The cells from one donor were tested in long-term killing assays (lower graph). LCL 0.174 cell lines were used: wildtype, SCNN1A knockout (using gRNA-1 and -2) and SCNN1A knock-in (KO cells that had received a codon optimized SCNN1A transgene) cells.

DETAILED DESCRIPTION

Methods and Materials

T-Cell Line Generation and Clonotyping

Figure 1A:
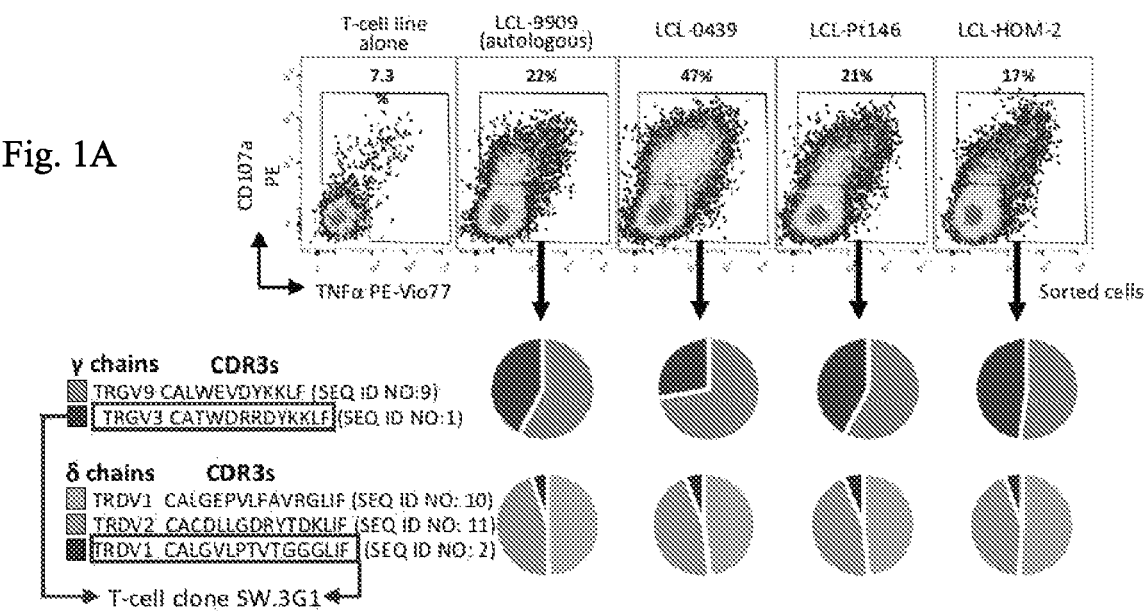
FIGS. 1A-1B show how a γδ T-cell line reactive to autologous and non-autologous lymphoblastoid cell lines (LCLs) was clonotyped and found to express a TCR comprised of the TRGV3 and TRDV1 genes with the CDR3s CATWDRRDYKKLF (SEQ ID NO: 1) and CALGVLPTVTGGGLIF (SEQ ID NO: 2), respectively. A clone was grown by limited dilution that expressed this TCR and named SW.3G1.

Peripheral blood mononuclear cells (PBMCs) were purified from the blood of a healthy donor (code 9909) by standard density gradient separation. The dominant population of γδ T-cells in peripheral blood express a Vγ9Vδ2 TCR and typically respond to antigens derived from bacteria. In order to enrich γδTCR+/Vδ2− T-cells thereby increasing the likelihood of finding cancer reactive T-cells, we modified a magnetic based purification protocol. The first adaptation was to stain the PBMCs with a PE conjugated anti-Vδ2 antibody (Ab) (clone B6, BioLegend, San Diego, CA). Next, γδ TCR+ T-cells were negatively enriched by positively removing γδ TCR− cells according the manufacturer's instructions (Miltheyi Biotec, Bergish Gladbach, Germany). The second adaptation involved adding anti-PE microbeads (Miltneyi Biotec) to the beads of the γδ TCR purification kit, thereby removing δ2+ cells at the same time as the γδ TCR− cells. The purified cells were co-incubated with irradiated (3000-3100 rad) LCLs from three donors that had been generated from PBMC by immortalizing B-cells with Epstein-Barr Virus (EBV). All LCLs were grown in R10 media (RPMI-1640, 10% heat-inactivated fetal calf serum, 2 mM L-glutamine, 100 U/mL Penicillin and 100 µg/mL Streptomycin, all Life Technologies, Carlsbad, CA) as suspension cells. After 14 days the T-cells were restimulated with irradiated LCLs from the same donors. On day 28 the T-cells were harvested and used in activation assays to assess reactivity towards LCLs. T-cells (30,000) were incubated for 4 h in 96 U well plates with an equivalent number of LCLs. 30 mM of the TNFα Processing Inhibitor-0 (TAPI-0 from Sigma Aldrich) (Haney et al., 2011), anti-CD107a Ab (H4A2, Becton Dickinson (BD), Franklin Lakes, NJ) and anti-TNFα Ab (cA2, Miltenyi Biotec) were added to the assay media at the start of the assay, with the cells subsequently stained with the cell viability dye, Vivid (Life Technologies, 1:40 dilution in PBS then 2 µL per stain in 50 µL) and anti-CD3 antibody (Ab) (BW264/56, Miltenyi Biotec). Activated cells were sorted on a BD FACS Aria in to RLT Plus buffer (supplemented with 40 mM DTT) (Qiagen) ready for sequencing of the TCR chains. RNA was extracted using the RNEasy Micro kit (Qiagen, Hilden, Germany). cDNA was synthesized using the 5'/3' SMARTer kit (Clontech, Paris, France) according to the manufacturer's instructions. The SMARTer approach used a Murine Moloney Leukaemia Virus (MMLV) reverse transcriptase, a 3' oligo-dT primer and a 5' oligonucleotide to generate cDNA templates, which were flanked by a known, universal anchor sequence. PCRs were performed using anchor-specific forward primers and reverse primers of the constant regions of the γ or δ TCR chains. The final PCR products were gel purified and prepared for next generation sequencing (Donia et al., 2017).

Clone SW.3G1 Procurement and Phenotyping

T-cells were cloned directly from the T-cell line by limiting dilution (Theaker et al., 2016). After 4 weeks of culture, 50% of each clone by culture volume was harvested and used for the activation assays with LCLs as above. Prior to performing activation assays, T-cell clones were washed and incubated for 24 h in reduced serum media. Clones that exhibited reactivity towards the LCLs were grown to sufficient numbers for TCR sequencing (below). Clone SW.3G1 was stained with Abs for surface expression of CD3 (Miltenyi Biotec), CD8 (BW135/80, Miltenyi Biotec), CD4 (M-T466, Miltenyi Biotec), αβ TCR (BW242/412, Miltenyi Biotec) and TCR Vδ1 chain (REA173, Miltenyi Biotec).

Sequencing of the SW.3G1 TCR

As above for sequencing the T-cell lines with the purified PCR products after the final PCR being cloned into Zero-Blunt TOPO and transformed into One Shot Chemically Competent E. coli cells for standard sequencing (both from Life Technologies).

SW.3G1 Recognized LCLs but not Healthy Cells

To confirm SW.3G1 reactivity towards LCLs, activation assays as above, and chromium release cytotoxicity assays were performed. Healthy B-cells were purified from donor 9909 using a PE conjugated anti-CD19 Ab (HIB19, Miltenyi Biotec) and positive capture with anti-PE microbeads (Miltenyi Biotec) and used immediately in assays. Other healthy cell lines and their proprietary culture media were obtained from Sciencell (Carlsbad, CA): CIL-1 (human non-pigmented ciliary epithelium) and Hep2 (human hepatocyte) were used in activation as above.

SW.3G1 Killed all Immortalized and Cancer Cell Lines Tested

LCLs and tumour cells were labelled with chromium 51 for cytotoxicity assays (Ekeruche-Makinde et al., 2012), with T-cell to target cell ratios of 1:1 (LCLs) or 10:1 (cancer cells). LCLs were maintained as above. Cancer cells lines (ATCC® reference for background and culture information)/tissue of origin: SiHa (HTB-35) and MS751 (HTB-34)/cervical; MCF7 (HTB-22), MDA-MB-231 (CRM-HTB-26) and SKBR3 (HTB-30)/breast; TK143 (CRL-8303) and U20S (HTB-96)/bone; HCT-116 (CCL-247) and Colo205 (CCL-222)/colon; Jurkat (TIB-152), K562 (CCL-243), THP-1 (TIB-202), U266 (TIB-196) and Molt-3 (CRL-1552)/blood; Caki-1 (HTB-46)/kidney; A549 (CCL-185) and H69 (HTB-119)/lung. MM909.11, MM909.12, MM909.15, MM909.46 and MM909.24 are skin melanomas obtained from cancer patients treated at the Center for Cancer Immune Therapy (CCIT, Herlev Hospital, Copenhagen, Denmark). The 'MM' cell lines and melanomas Mel 526 and Mel 624 were maintained as adherent cells in R10, passaged once weekly or when required, aiming for 20-80% confluence. Cells were detached from tissue culture flasks by rinsing with D-PBS followed by incubation with D-PBS and 2 mM EDTA at 37° C. until detached.

SW.3G1 Did not Recognize Target Cells by Known Mechanisms

The Vγ9Vδ2 T-cell activator (E)-4-Hydroxy-3-methyl-but-2-enyl pyrophosphate (HMB-PP) (Sigma Aldrich) was reconstituted in DMSO and added directly to assay wells. The following monoclonal Abs were used for blocking assays: anti-HLA, -B, -C (clone W6/32, Biolegend), anti-HLA-DR, -DP, -DQ (clone Tu39, Bioloegend), anti-EPCR (polyclonal, R&D systems), anti-MICA/MICB (clone 6D4, BioLegend) and anti-CD1d (clone 51.1, Miltenyi Biotech) were used at a final concentration of 10 µg/m L.

Gene Trapping by Whole Genome CRISPR

Figure 5A:
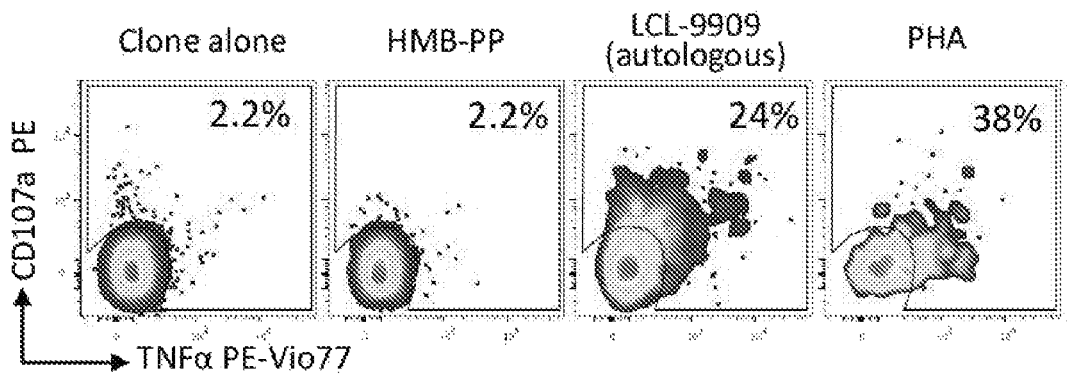
FIGS. 5A-5B show that SW.3G1 does not recognize target cells by known mechanisms.

A whole genome CRISPR/Cas9 library approach was used (FIG. 5 for an overview). Whole genome targeted LCL-9909 and KBM7s using the GeCKO v2 sub-libraries A and B (Adgene plasmid, #1000000048, kindly provided by Dr. Feng Zhang (Patel et al., 2017)) were used for selection by SW.3G1. Briefly, successfully transduced target cells selected with puromycin were co-incubated with SW.3G1 at a predefined ratio for 2-3 weeks in 96 U well plates. Activation assays (as above) were performed with pre- and post-selected target cells to confirm loss of SW.3G1 activity towards the selected cells. Genomic DNA from the target cells that had survived two rounds of selection with SW.3G1 was used for next generation sequencing to reveal inserted guide RNAs and candidate genes.

Confirming SCNN1A Role in Target Cell Recognition

Lentiviral particles were generated by calcium chloride transfection of HEK 293T cells and concentrated by ultracentrifugation prior to transduction of target cells using 8 µg/mL of polybrene and spinfection. gRNAs were cloned into the pLentiCRISPR v2 plasmid (kindly provided by Dr. Feng Zhang, Addgene plasmid 52961), which encodes the SpCas9 protein and a puromycin resistance marker gene (pac, puromycin N-acetyltransferase), and co-transfected with packaging and envelope plasm ids pMD2.G and psPAX2 (all from Addgene). Full-length codon optimized SCNN1A transgene (Isoform 1, UniProt P37088-1) was cloned in to a $3^{rd}$ generation lentiviral transfer vector pELNS (kindly provided by Dr. James Riley, University of Pennsylvania, PA). The pELNS vector contains rat CD2 (rCD2) gene for selection of cells using an anti-rCD2 PE Ab (OX-34, BioLegend). SCNN1A expression in target cells was assessed using the rabbit anti-SCNN1A polyclonal antibody (PA1-902A, ThermoFisher Scientific) for flow cytometry (data not sown) and western blot analysis according to the manufacturer's instructions.

Transduction of Polyclonal T-Cells with the SW.3G1 TCR Confers Target Cell Recognition Codon optimized, full length TCR chains, separated by a self-cleaving 2A sequence, were synthesized (Genewiz) and cloned into the 3rd generation lentiviral transfer vector pELNS (kindly provided by Dr. James Riley, University of Pennsylvania, PA). The pELNS vector contains a rat CD2 (rCD2) marker gene separated from the TCR by another self-cleaving 2A sequence. Additionally, cells were co-transduced with a gRNA to ablate TCRβ chain expression in recipient cells by targeting both TCR-β constant domains (manuscript currently at Blood for publication). Lentiviral particles were generated by calcium chloride transfection of HEK293T cells. TCR transfer vectors were co-transfected with packaging and envelope plasmids pMD2.G, pRSV-Rev and pMDLg/pRRE. Lentiviral particles were concentrated by ultracentrifugation prior to transduction of CD8+ T-cells using 5 μg/ml of polybrene, with the CD8+ T-cells purified by magnetic separation (Miltenyi Biotec) from three healthy donors 24 h in advance and activated overnight with CD3/CD28 beads (Dynabeads, Life Technologies) at 3:1 bead:T-cell ratio. T-cells that had taken up the virus were selected by incubation with 2 μg/ml puromycin (TCRβ chain knockout) and enriched with anti-rCD2 PE Ab (OX-34, BioLegend) followed by anti-PE magnetic beads (Miltenyi Biotec). 14 d post transduction T-cells were expanded with allogeneic feeders and PHA. TCR transduced cells were used in longterm killing assays whereby LCL.174 targets were plated in duplicate at the density of 50,000 cells/well in 96 U well plates. SW.3G1 was added to the target and incubated for 7 days. Target cells were also plated without T-cells, to serve as a 100% survival control. Cells were harvested, washed with PBS, and stained with Vivid and anti-CD3 antibody (to exclude T-cells). As an internal control, CountBright™ Absolute Counting Beads (Life Technologies) were added to each well prior to harvesting/washing (approximately 10,000 beads/well). The samples were the acquired on FACS Canto II, and at least 1,000 bead events were acquired per sample. The survival of target cells was calculated according to the following formula:

$$\% \text{ survival} = \frac{\text{number of experimental cell events/number of experimental bead events}}{\text{number of control cell events/number of control bead events}} \times 100\%$$

Results

Clone Characterisation

1. Purified γδ T-cells from a healthy donor (9909) primed and re-stimulated with a pool of three non-autologous lymphoblastoid cell lines (-0439, -pt146 and -HOM-2). Reactivity towards each of the cells lines was tested at day 28 (FIG. 1). The T-cell line also recognized autologous LCL-9909 (FIG. 1).

2. T-cells from the aforementioned line were flow cytometry sorted based on reactivity to each of the LCLs and their TCRs analysed by next generation sequencing (FIG. 1). For the γ-chain sequencing, two unique CDR3s were present with variable chains TRGV9 and TRGV3. For the δ-chains, three CDR3s were present with variable chains TRDV1 and TRDV2.

3. T-cells clones procured from the donor 9909 T-cell line expressed a γ3δ1 TCR and CDR3s CATWDRRDYKKL and CALGVLPTVTGGGLIF for each respective chain (FIG. 1 and FIG. 2). All the clones that grew expressed the same TCR. This clone was named SW.3G1.

Figure 1B:
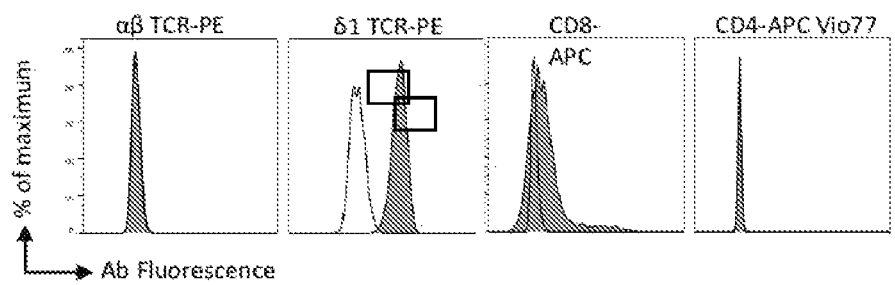
Figure 2:
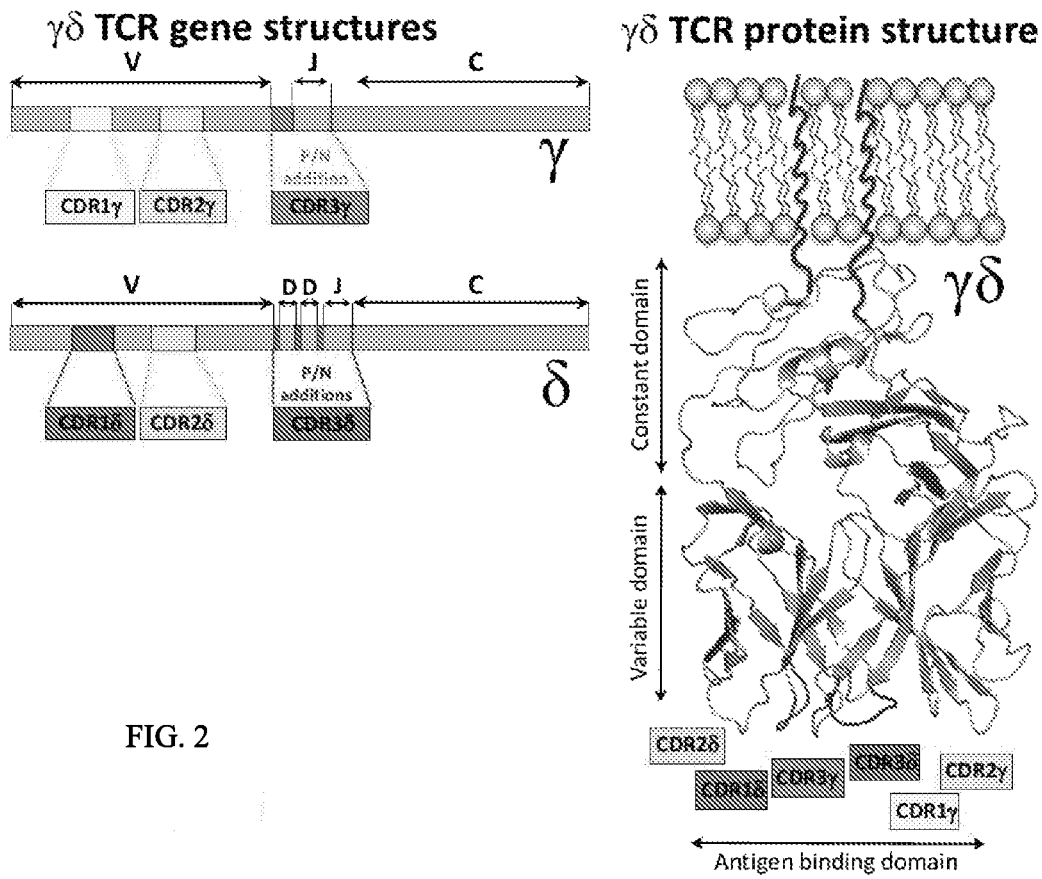
FIG. 2 shows the T-cell receptor sequence of the γ and δ TCR chains of clone SW.3G1. The mRNA structures (top) show that for each chain CDR1 and CDR2 are encoded in the germline. CDR3 is the product of junctional diversity at V-J joins of T cell receptor (TCR)-γ chain and V-D-J joins in TCR-S chain. CDR3 is consequently hypervariable. The colour code adopted for the CDR loops is maintained throughout the figure. The areas coloured in grey represent the constant and variable domains of the TCRs (not including the hypervariable CDR loops). The panel on the right shows the expected protein fold. TCRs adopt similar tertiary structures that position the complementarity-determining regions (CDR) loops at the membrane distal end of the molecules. Together the six CDR loops form the antigen binding site.

Ab staining of SW.3G1 confirmed expression of the Vδ1 chain, and αβ TCR-/CD8 low/CD4- (FIG. 1B).

4. Activation assays using TNFα and CD107a as the readouts confirmed SW.3G1 reactivity towards autologous LCL-9909 and non-autologous LCL-0439 (FIG. 3A). Donors 9909 and 0439 are completely HLA mismatched for both MHC class I and class II alleles, therefore SW.3G1 is recognizing target cells in an HLA-independent manner. SW.3G1 was also able to lyse LCL-9909 and -0439 and is therefore cytotoxic (FIG. 3B). The recognition of the LCLs was dependent on the immortalization process when EBV infects a B-cell, as autologous healthy B-cells purified directly ex-vivo from 9909 did not act as targets for SW.3G1 (FIG. 3C). Similarly, the healthy cells CIL-1 (epithelial cell) and Hep2 (hepatocyte) did not elicit SW.3G1 activation (FIG. 3D).

Figure 4A:
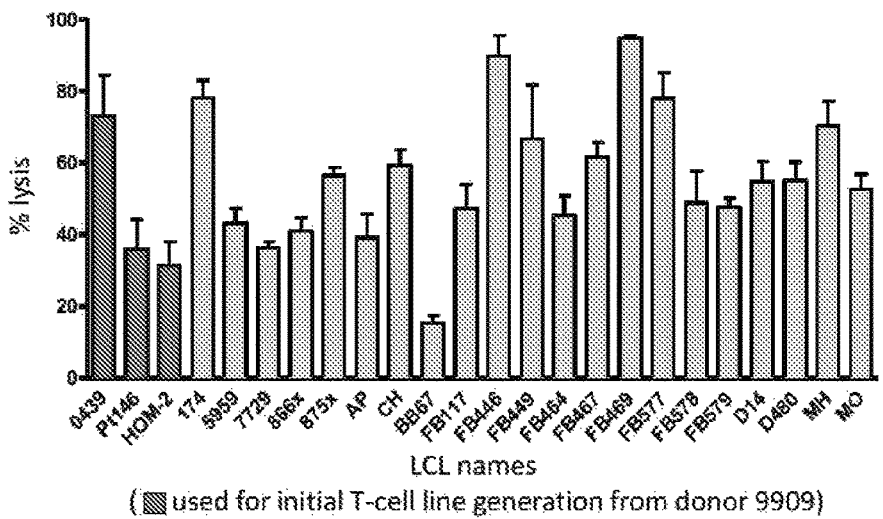
FIGS. 4A-4B show SW.3G1 mediated lysis of LCLs from multiple donors that share no common HLA and an array of cancer cell lines from different tissues. SW.3G1 was used in 6.5 h chromium release cytotoxicity assays.

5. SW.3G1 was able to lyse LCLs from all 24 donors tested (FIG. 3B for the autologous LCL and FIG. 4A for 23 non-autologous LCLs) providing further confirmation that SW.3G1 is acting in a HLA independent manner. Furthermore, LCL 0.174 (FIG. 4A, 4th bar from the left) only expresses one copy of chromosome 6, the human chromosome that carries the MHC locus. The chromosome 6 in cell LCL 0.174 contains a large deletion and does not carry genes for MHC class II and many components involved in MHC class I antigen processing.

Figure 4B:
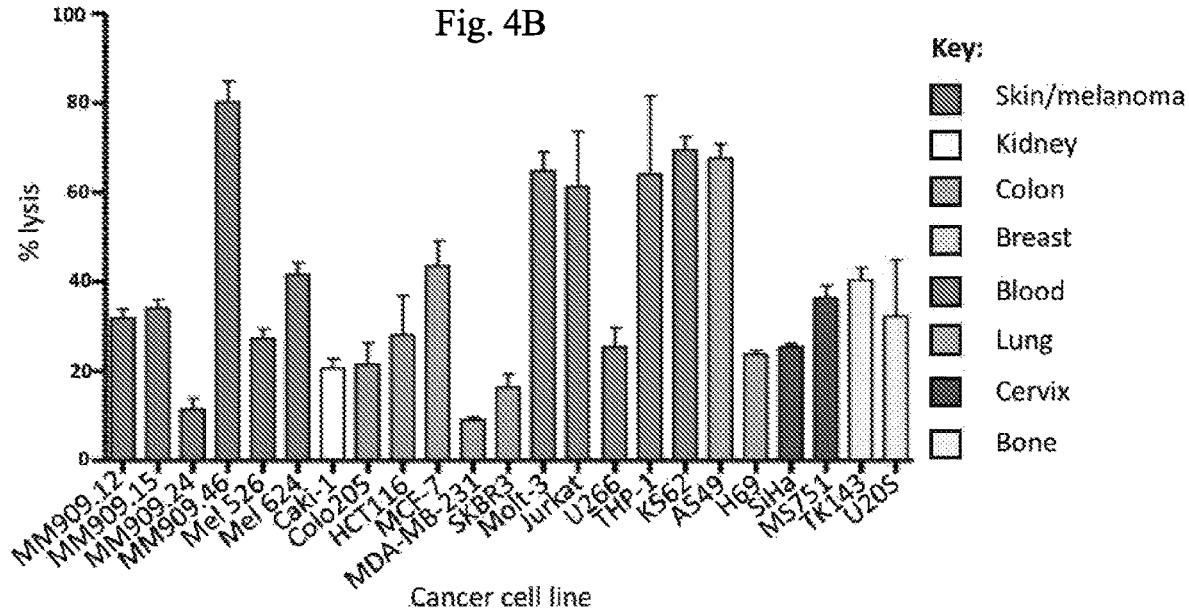

6. SW.3G1 killed 23 cancer cell lines that originate from 8 different tissues: skin/melanoma, kidney, colon, breast, blood/leukemia, lung, cervix and bone. (FIG. 4B).

Figure 5B:
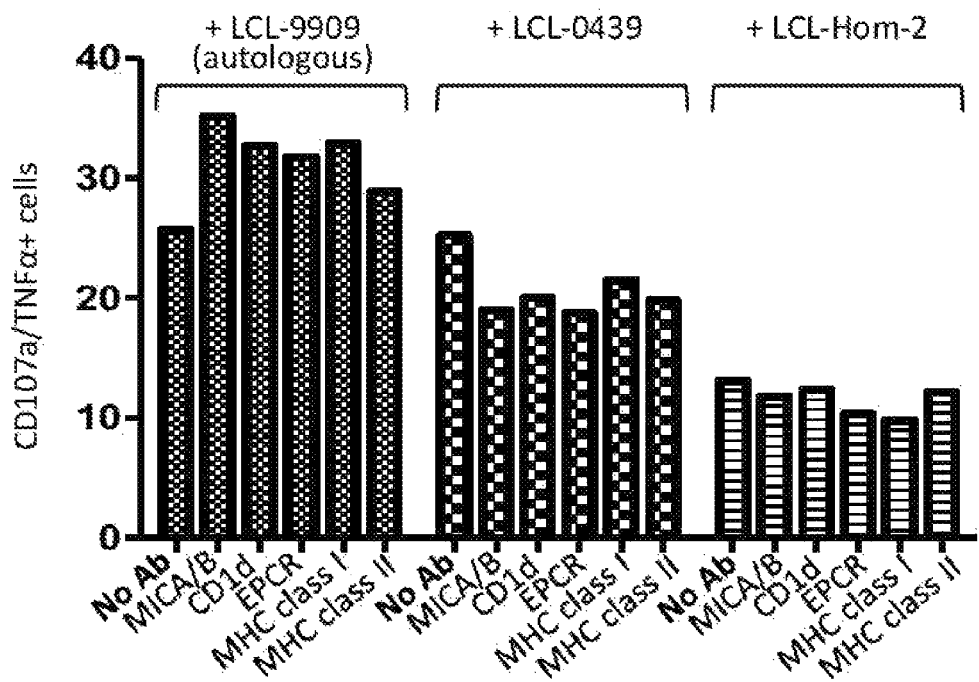
Figure 6:
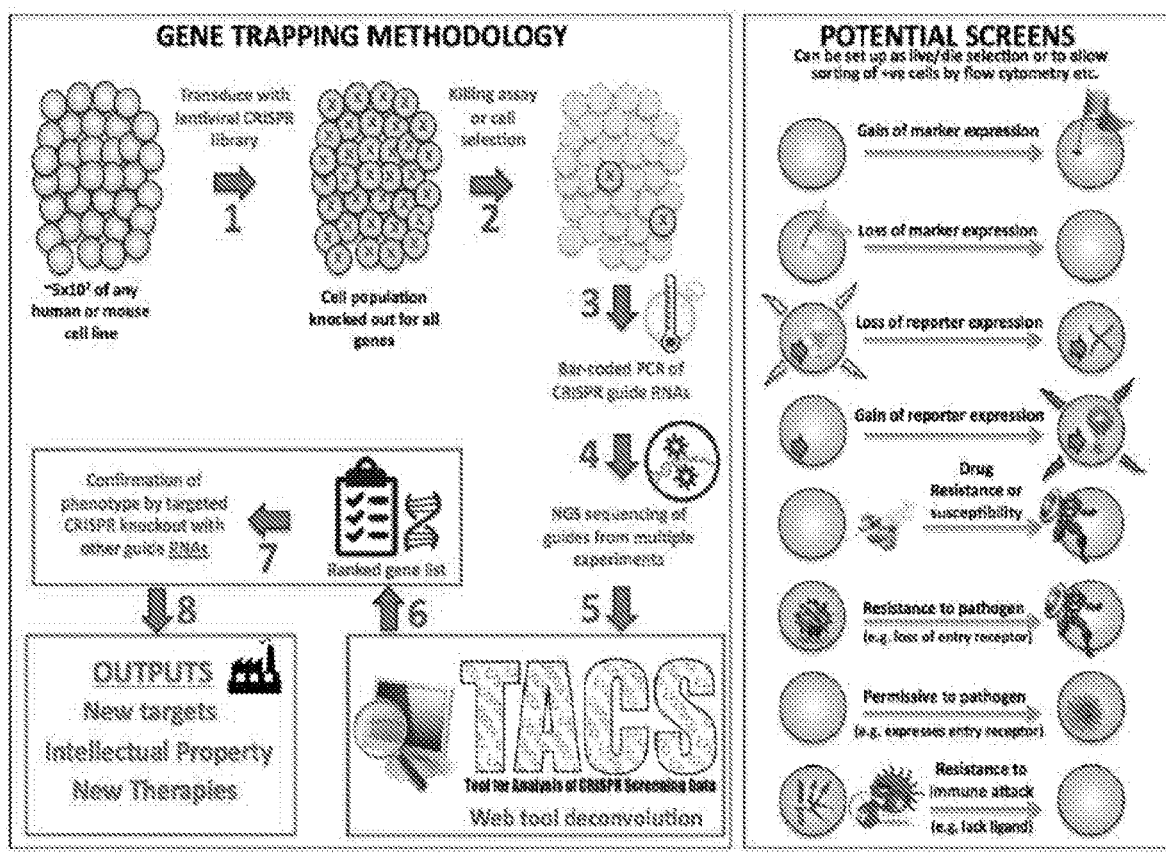
FIG. 6 shows the whole genome CRISPR/Cas9 approach used to identify candidate genes/proteins involved in target cell recognition by SW.3G1.

7. SW.3G1 did not respond to the known γδ T-cell antigen, HMB-PP (FIG. 5A), which leads to recognition of pathogen infected cells by the Vγ9Vδ2 TCR T-cell subset in a similar manner to recognition of the self pyrophosphate. This pathway requires target cells to express Butyrophillin 3A1. SW.3G1 reactivity towards LCL-9909 (autologous) -0439 and -pt146 was not hindered by inclusion of blocking antibodies that bind known γδ T-cell ligands: Major Histocompatibility Complex (MHC) Class-I related chain A and B (MICA/MICB), EPCR Endothelial Protein C Receptor (EPCR) and CD1d (FIG. 5B). MHC class I and class II also failed to block SW.3G1 activation. Although not an extensive exclusion process, these data suggested that SW.3G1 might recognize an unknown γδ TCR ligand at the surface of cancer cells. Therefore, a whole genome CRISPR/Cas9 library approach was adopted to find candidate genes/proteins involved in SW.3G1 recognition of target cells (FIG. 6).

8. Whole genome CRISPR/Cas9 libraries were used to create gene knockouts in autologous LCL-9909 and the haploid myeloid leukaemia cell line KBM7. Both libraries were co-incubated with SW.3G1 for successive rounds of selection to enrich for target cells containing gRNAs that allowed escape from SW.3G1-mediated lysis (FIG. 7A). SW.3G1 reactivity dropped from 59% for pre-selected LCL-9909 to 12% post-selection. For KMB7s reactivity went from 12% to 4.2%. The post-selected LCL-9909s and KBM7s were used for next generation sequencing to identify gRNAs that had been enriched. Key genes were identified with 4 of the total 7 genes shared between the LCL-9909 and KBM7 libraries (FIGS. 7B and 7C). Guides specific for the gene SCNN1A (also used here to describe the encoded protein), which encodes for the protein Sodium Channel Epithelial 1 Alpha Subunit, were highly enriched present in both libraries (FIGS. 7B&C). SCNN1A gene and protein aliases are shown in FIG. 8. The protein is cell surface expressed and therefore a good candidate for further exploration. SCNN1A has 6 splice variant isoforms and various naturally occurring mutations (FIGS. 8 and 9).

Figure 10A:
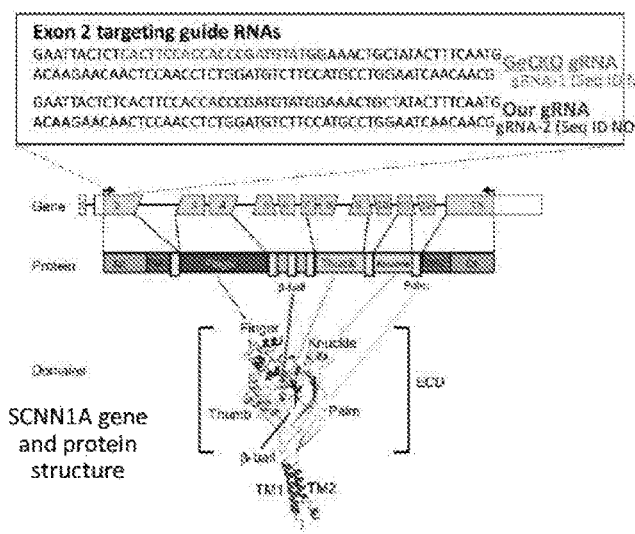
FIGS. 10A-10D show the results of experiments to validate the role of SCNN1A in target cell recognition by SW.3G1.
Figure 10B:
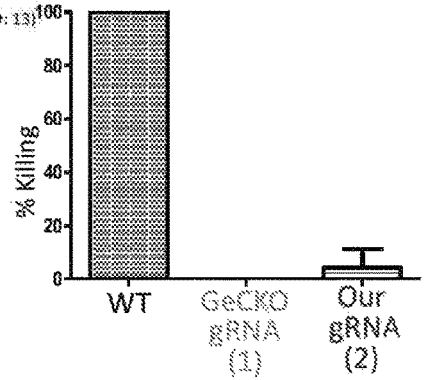
Figure 10C:
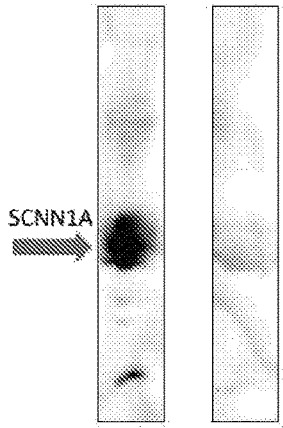
Figure 10D:
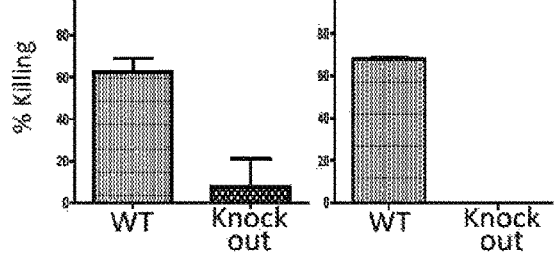

9. LCL.174 transduced with SCNN1A gRNA from the whole genome library (GeCKO, gRNA-1) or a different guide designed in-house (gRNA-2) (FIG. 10A) were no longer targets of SW.3G1, thereby confirming SCNN1A's role in target cell recognition (FIG. 10B), with lysis falling to below 5% for the knockout cell lines compared to 100% killing for the wildtype cells. SCNN1A gene knockout lines were created in two cancer cells, which either partially or completely escaped lysis by SW.3G1 (FIG. 10C). It is noteworthy that the SCNN1A knockout cells created throughout this study were used as lines, and not cloned before performing assays. This may account for the residual reactivity seen for some of the 'knockout' cell lines as a minority proportion of the cells within a knockout line probably still express SCNN1A, due to escape from puromycin selection and/or unsuccessful ablation of the SCNN1A gene. Western blot analysis of the SCNN1A knockout MDA-MB-231 cells used for SW.3G1 activation assays revealed a substantial reduction of the SCNN1A protein in the knockout cell line compared to the wildtype cells (FIG. 10C) confirming the gene knockout. The Ab used can recognise all SCNN1A isoforms (FIG. 9). We also noted that the SCNN1A knockout cells became less viable with extensive culture (3+ weeks) and in some cases cell division halted completely. This observation was unique to the SCNN1A gRNA as the same cell lines transduced with gRNAs for many other genes did not exhibit the same change in cell growth and vitality. This result suggested that the SCNN1A gene is essential for long-term growth of cells in culture.

Figure 11A:
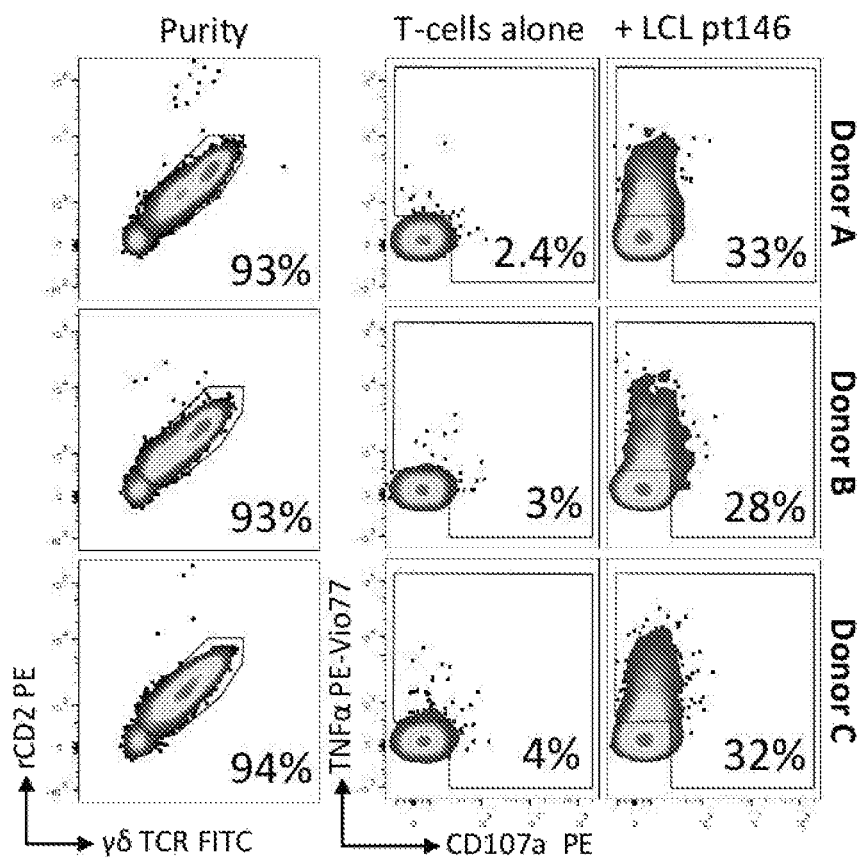
FIGS. 11A-11B shows that transfer of the TCR from SW.3G1 confers target cell reactivity to αβ T-cells from three healthy donors.
Figure 11B:
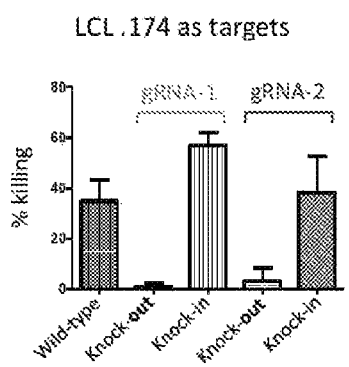

10. Transfer of the SW.3G1 TCR in to polyclonal CD8+ T-cells from three healthy donors conferred reactivity to target cell LCL-pt146 (FIG. 11A). TCR transduced cells exhibited the same functional profile to SCNN1A knockout cells as described above for the SW.3G1 clone (FIG. 11B). To compliment the SCNN1A knockout data, and to further confirm the role of SCNN1A in target cell recognition, we transduced the knockout cells with the SCNN1A gene. The introduction of a native SCNN1A gene to knockout cells expressing the SCNN1A gRNAs would lead to gene ablation of the transgene. Therefore, a codon-optimized gene was introduced, different to the DNA sequence of the native gene (Isoform 1 UniProt P37088-1, FIG. 9), but expressing the same protein. Killing of the gRNA-1 or gRNA-2 transduced cells was ablated but could be restored by expressing the SCNN1A gene in the knockout cells (FIG. 11B).

CONCLUSION

The SW.3G1 TCR enables T-cells to recognise a wide range of tumours. Recognition occurs via the SCNN1A gene product. SW.3G1 T-cell clone recognises a cancer-cell specific SCNN1A ligand in the absence of MHC restriction.

This invention centres around the TCR identified in T-cell clone SW.3G1. This TCR recognises a wide range of cancer cells through the expression of SCNN1A. This TCR does not recognise non-tumour cells. CRISPR/Cas9 knockout of SCNN1A from tumour lines or antibody blocking confirmed there TCR requires the SCNN1A gene product for recognition of tumour cells. The SW.3G1 TCR can be used in a variety of different cancer immunotherapy strategies. The broad tumour recognition and human leukocyte antigen (HLA)-independence of recognition unlocks exciting possibilities for pan-cancer, pan-population immunotherapies using this TCR.

REFERENCES

Chen, J., T R Kleyman and S. Sheng. 2014 Deletion of α-subunit exon 11 of the epithelial Na+ channel reveals a regulatory module. Am J Physiol. Renal Physiol 306, F561-7.

Donia, M., Kjeldsen, J. W., Andersen, R., Westergaard, M. C. W., Bianchi, V., Legut, M., Attaf, M., Szomolay, B., Ott, S., Dolton, G., Lyngaa, R., Hadrup, S. R., Sewell, A. K., Svane, I. M., 2017. PD-1+ polyfunctional T cells dominate the periphery after tumor-infiltrating lymphocyte therapy for cancer. Clin. Cancer Res. clincanres. 1692.2016.

Ekeruche-Makinde, J., Clement, M., Cole, D. K., Edwards, E. S. J., Ladell, K., Miles, J. J., Matthews, K. K., Fuller, A., Lloyd, K. A., Madura, F., Dolton, G. M., Pentier, J., Lissina, A., Gostick, E., Baxter, T. K., Baker, B. M., Rizkallah, P. J., Price, D. A., Wooldridge, L., Sewell, A. K., 2012. T-cell receptor-optimized peptide skewing of the T-cell repertoire can enhance antigen targeting. J. Biol. Chem. 287, 37269-81.

Haney, D., Quigley, M. F., Asher, T. E., Ambrozak, D. R., Gostick, E., Price, D. A., Douek, D. C., Betts, M. R., 2011. Isolation of viable antigen-specific CD8+ T cells based on membrane-bound tumor necrosis factor (TNF)-alpha expression. J. Immunol. Methods 369, 33-41.

Legut, M., G Dolton, A. A. Mian, O. Ottmann and A. K. Sewell. 2017 CRISPR-mediated TCR replacement generates superior anticancer transgenic T-cells. Blood [Epub ahead of print] doi: https://doi.org/10.1182/blood-2017-05-787598

Patel, S. J., Sanjana, N. E., Kishton, R. J., Eidizadeh, A., Vodnala, S. K., Cam, M., Gartner, J. J., Jia, L., Steinberg, S. M., Yamamoto, T. N., Merchant, A. S., Mehta, G. U., Chichura, A., Shalem, O., Tran, E., Eil, R., Sukumar, M., Guijarro, E. P., Day, C.-P., Robbins, P., Feldman, S., Merlino, G., Zhang, F., Restifo, N. P., 2017. Identification of essential genes for cancer immunotherapy. Nature 548, 537-542.

Theaker, S. M., Rius, C., Greenshields-Watson, A., Lloyd, A., Trimby, A., Fuller, A., Miles, J. J., Cole, D. K., Peakman, M., Sewell, A. K., Dolton, G., 2016. T-cell libraries allow simple parallel generation of multiple peptide-specific human T-cell clones. J. Immunol. Methods 430, 43-50.

The invention claimed is:

1. A vector encoding a tumour specific T-cell receptor (TCR), wherein the TCR comprises (i) a γ chain having three γ chain complementarity-determining regions (CDRs) comprising the sequences: VTNTFY (SEQ ID NO: 3) as CDR1γ, YDVSTARD (SEQ ID NO: 4) as CDR2γ and CATWDRRDYKKLF (SEQ ID NO: 1) as CDR3γ and (ii) a δ chain having three δ chain CDRs comprising the sequences: TSWWSYY (SEQ ID NO: 5) as CDR1δ, QGS (SEQ ID NO: 6) as CDR2δ and CALGVLPTVTGGGLIF (SEQ ID NO: 2) as CDR3δ.

2. The vector according to claim 1, wherein said γ chain comprises the amino acid sequence:
SSNLEGRTKSVTRQTGSSAEITCDLTVTNTFYIHWYLHQEGKAPQRLLYYDVSTARD VLESGLSPGKYYTHTPRRWSWILRLQNLIENDSGVYYCATWDRRDYKKLFGSGTTV VTDKQLDADVSPKPTIFLPSIAETKLQKAGTYLCLLEKFFPDVIKIHWQEKKSNTILS QEGNTMKTNDTYMKFSWLTVPEKSLDKEHRCIVRHENNKNGVDQEIIFPPIKT (SEQ ID NO:7) or a sequence that shares at least 95% identity therewith.

3. The vector according to claim 1, wherein said δ chain comprises the amino acid sequence of:
AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGVLPTVTGGGLIFGKGTRT VEPNSQPHTKPSVFVMKNGTNVACLVKEFYPKDIRINLVSSKKITEFDPAIVISPSGY NAVKLGKYEDSNSVTCSVQHDNKTVHSTDFEVKTDST (SEQ ID NO:8) or a sequence that shares at least 95% identity therewith.

4. A T-cell comprising a vector encoding a tumour specific TCR, wherein the TCR comprises (i) a γ chain having three γ chain CDRs comprising the sequences: VTNTFY (SEQ ID NO: 3) as CDR1γ, YDVSTARD (SEQ ID NO: 4) as CDR2γ and CATWDRRDYKKLF (SEQ ID NO: 1) as CDR3γ and (ii) a δ chain having three δ chain CDRs comprising the sequences: TSWWSYY (SEQ ID NO: 5) as CDR1δ, QGS (SEQ ID NO: 6) as CDR2δ and CALGVLPTVTGGGLIF (SEQ ID NO: 2) as CDR3δ and wherein the T cell expresses said TCR.

5. A pharmaceutical composition comprising the T cell according to claim 4.

6. A method of treating cancer in an individual to be treated comprising administering to said individual the T cell according to claim 4.

7. The method according to claim 6, wherein said cancer is selected from the group consisting of colorectal cancer, lung, kidney, prostrate, bladder, cervical, skin melanoma, bone, breast, blood cancer, brain, pancreas, testicle, ovary, head/neck, liver, bladder, thyroid, and uterine.

8. The method according to claim 6, wherein said T cell is administered in combination with an anti-tumour agent.

9. The vector encoding the tumour specific TCR according to claim 1, wherein said TCR binds to at least one SCNNA1 gene product isoform amino acid sequence set forth in SEQ ID NOs: 14 to 19.

10. The vector encoding the tumour specific TCR according to claim 9, wherein said TCR binds to the extracellular domain of said isoform.

11. The vector according to claim 1, wherein the TCR is a chimeric TCR.

12. The vector according to claim 1, which is a lentiviral vector.

13. The vector according to claim 2, wherein said δ chain comprises the amino acid sequence of:
AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGVLPTVTGGGLIFGKGTRT VEPNSQPHTKPSVFVMKNGTNVACLVKEFYPKDIRINLVSSKKITEFDPAIVISPSGK YNAVKLGKYEDSNSVTCSVQHDNKTVHSTDFEVKTDST (SEQ ID NO:8) or a sequence that shares at least 95% identity therewith.

14. The vector according to claim 13, wherein said γ chain comprises the sequence of SEQ ID NO: 7 or a sequence that shares at least 98% identity therewith and said δ chain comprises the sequence of SEQ ID NO: 8 or a sequence that shares at least 98% identity therewith.

15. The vector according to claim 13, which is a lentiviral vector.

16. The T-cell according to claim 4, wherein said γ chain comprises the amino acid sequence:
SSNLEGRTKSVTRQTGSSAEITCDLTVTNTFYIHWYLHQEGKAPQRLLYYDVSTARD VLESGLSPGKYYTHTPRRWSWILRLQNLIENDSGVYYCATWDRRDYKKLFGSGTTV VTDKQLDADVSPKPTIFLPSIAETKLQKAGTYLCLLEKFFPDVIKIHWQEKKSNTILS QEGNTMKTNDTYMKFSWLTVPEKSLDKEHRCIVRHENNKNGVDQEIIFPPIKT (SEQ ID NO:7) or a sequence that shares at least 95% identity therewith; and
wherein said δ chain comprises the amino acid sequence of:
AQKVTQAQSSVSMPVRKAVTLNCLYETSWWSYYIFWYKQLPSKEMIFLIRQGSDEQ NAKSGRYSVNFKKAAKSVALTISALQLEDSAKYFCALGVLPTVTGGGLIFGKGTRT VEPNSQPHTKPSVFVMKNGTNVACLVKEFYPKDIRINLVSSKKITEFDPAIVISPSGK YNAVKLGKYEDSNSVTCSVQHDNKTVHSTDFEVKTDST (SEQ ID NO:8) or a sequence that shares at least 95% identity therewith.

17. The T-cell according to claim 16, wherein said vector is a lentiviral vector.

18. A method of treating cancer in an individual to be treated comprising administering to said individual the T-cell according to claim 16.

19. The method according to claim 18, wherein said cancer is selected from the group consisting of colorectal cancer, lung, kidney, prostrate, bladder, cervical, skin melanoma, bone, breast, blood cancer, brain, pancreas, testicle, ovary, head/neck, liver, bladder, thyroid, and uterine.

20. A pharmaceutical composition comprising the vector according to claim 1.

* * * * *

SEQUENCE LISTING

<160> NUMBER OF SEQ ID NOS: 19

<210> SEQ ID NO 1
<211> LENGTH: 13
<212> TYPE: PRT
<213> ORGANISM: Homo sapiens

<400> SEQUENCE: 1

Cys Ala Thr Trp Asp Arg Arg Asp Tyr Lys Lys Leu Phe
1               5                   10

<210> SEQ ID NO 2
<211> LENGTH: 16

```
<212> TYPE: PRT
<213> ORGANISM: Homo sapiens

<400> SEQUENCE: 2

Cys Ala Leu Gly Val Leu Pro Thr Val Thr Gly Gly Gly Leu Ile Phe
1               5                   10                  15

<210> SEQ ID NO 3
<211> LENGTH: 6
<212> TYPE: PRT
<213> ORGANISM: Homo sapiens

<400> SEQUENCE: 3

Val Thr Asn Thr Phe Tyr
1               5

<210> SEQ ID NO 4
<211> LENGTH: 8
<212> TYPE: PRT
<213> ORGANISM: Homo sapiens

<400> SEQUENCE: 4

Tyr Asp Val Ser Thr Ala Arg Asp
1               5

<210> SEQ ID NO 5
<211> LENGTH: 7
<212> TYPE: PRT
<213> ORGANISM: Homo sapiens

<400> SEQUENCE: 5

Thr Ser Trp Trp Ser Tyr Tyr
1               5

<210> SEQ ID NO 6
<211> LENGTH: 3
<212> TYPE: PRT
<213> ORGANISM: Homo sapiens

<400> SEQUENCE: 6

Gln Gly Ser
1

<210> SEQ ID NO 7
<211> LENGTH: 226
<212> TYPE: PRT
<213> ORGANISM: Homo sapiens

<400> SEQUENCE: 7

Ser Ser Asn Leu Glu Gly Arg Thr Lys Ser Val Thr Arg Gln Thr Gly
1               5                   10                  15

Ser Ser Ala Glu Ile Thr Cys Asp Leu Thr Val Thr Asn Thr Phe Tyr
            20                  25                  30

Ile His Trp Tyr Leu His Gln Glu Gly Lys Ala Pro Gln Arg Leu Leu
        35                  40                  45

Tyr Tyr Asp Val Ser Thr Ala Arg Asp Val Leu Glu Ser Gly Leu Ser
    50                  55                  60

Pro Gly Lys Tyr Tyr His Thr Pro Arg Arg Trp Ser Trp Ile Leu
65                  70                  75                  80

Arg Leu Gln Asn Leu Ile Glu Asn Asp Ser Gly Val Tyr Tyr Cys Ala
                85                  90                  95

Thr Trp Asp Arg Arg Asp Tyr Lys Lys Leu Phe Gly Ser Gly Thr Thr
```

```
                    100                 105                 110
Leu Val Val Thr Asp Lys Gln Leu Asp Ala Asp Val Ser Pro Lys Pro
            115                 120                 125

Thr Ile Phe Leu Pro Ser Ile Ala Glu Thr Lys Leu Gln Lys Ala Gly
            130                 135                 140

Thr Tyr Leu Cys Leu Leu Glu Lys Phe Phe Pro Asp Val Ile Lys Ile
145                 150                 155                 160

His Trp Gln Glu Lys Lys Ser Asn Thr Ile Leu Gly Ser Gln Glu Gly
                165                 170                 175

Asn Thr Met Lys Thr Asn Asp Thr Tyr Met Lys Phe Ser Trp Leu Thr
            180                 185                 190

Val Pro Glu Lys Ser Leu Asp Lys Glu His Arg Cys Ile Val Arg His
            195                 200                 205

Glu Asn Asn Lys Asn Gly Val Asp Gln Glu Ile Ile Phe Pro Pro Ile
            210                 215                 220

Lys Thr
225

<210> SEQ ID NO 8
<211> LENGTH: 209
<212> TYPE: PRT
<213> ORGANISM: Homo sapiens

<400> SEQUENCE: 8

Ala Gln Lys Val Thr Gln Ala Gln Ser Ser Val Ser Met Pro Val Arg
1               5                   10                  15

Lys Ala Val Thr Leu Asn Cys Leu Tyr Glu Thr Ser Trp Trp Ser Tyr
            20                  25                  30

Tyr Ile Phe Trp Tyr Lys Gln Leu Pro Ser Lys Glu Met Ile Phe Leu
            35                  40                  45

Ile Arg Gln Gly Ser Asp Glu Gln Asn Ala Lys Ser Gly Arg Tyr Ser
        50                  55                  60

Val Asn Phe Lys Lys Ala Ala Lys Ser Val Ala Leu Thr Ile Ser Ala
65                  70                  75                  80

Leu Gln Leu Glu Asp Ser Ala Lys Tyr Phe Cys Ala Leu Gly Val Leu
                85                  90                  95

Pro Thr Val Thr Gly Gly Gly Leu Ile Phe Gly Lys Gly Thr Arg Val
            100                 105                 110

Thr Val Glu Pro Asn Ser Gln Pro His Thr Lys Pro Ser Val Phe Val
            115                 120                 125

Met Lys Asn Gly Thr Asn Val Ala Cys Leu Val Lys Glu Phe Tyr Pro
            130                 135                 140

Lys Asp Ile Arg Ile Asn Leu Val Ser Ser Lys Lys Ile Thr Glu Phe
145                 150                 155                 160

Asp Pro Ala Ile Val Ile Ser Pro Ser Gly Lys Tyr Asn Ala Val Lys
            165                 170                 175

Leu Gly Lys Tyr Glu Asp Ser Asn Ser Val Thr Cys Ser Val Gln His
            180                 185                 190

Asp Asn Lys Thr Val His Ser Thr Asp Phe Glu Val Lys Thr Asp Ser
            195                 200                 205

Thr

<210> SEQ ID NO 9
<211> LENGTH: 12
<212> TYPE: PRT
```

<213> ORGANISM: Homo sapiens

<400> SEQUENCE: 9

Cys Ala Leu Trp Glu Val Asp Tyr Lys Lys Leu Phe
1               5                   10

<210> SEQ ID NO 11
<211> LENGTH: 16
<212> TYPE: PRT
<213> ORGANISM: Homo sapiens

<400> SEQUENCE: 10

Cys Ala Leu Gly Glu Pro Val Leu Phe Ala Val Arg Gly Leu Ile Phe
1               5                   10                  15

<210> SEQ ID NO 11
<211> LENGTH: 16
<212> TYPE: PRT
<213> ORGANISM: Homo sapiens

<400> SEQUENCE: 11

Cys Ala Cys Asp Leu Leu Gly Asp Arg Tyr Thr Asp Lys Leu Ile Phe
1               5                   10                  15

<210> SEQ ID NO 12
<211> LENGTH: 104
<212> TYPE: DNA
<213> ORGANISM: Homo sapiens

<400> SEQUENCE: 12
gaattactct cacttccacc acccgatgta tggaaactgc tatactttca atgacaagaa     60
caactccaac ctctggatgt cttccatgcc tggaatcaac aacg                    104

<210> SEQ ID NO 13
<211> LENGTH: 104
<212> TYPE: DNA
<213> ORGANISM: Homo sapiens

<400> SEQUENCE: 13
gaattactct cacttccacc acccgatgta tggaaactgc tatactttca atgacaagaa     60
caactccaac ctctggatgt cttccatgcc tggaatcaac aacg                    104

<210> SEQ ID NO 14
<211> LENGTH: 669
<212> TYPE: PRT
<213> ORGANISM: Homo sapiens

<400> SEQUENCE: 14

Met Glu Gly Asn Lys Leu Glu Glu Gln Asp Ser Ser Pro Gln Ser
1               5                   10                  15

Thr Pro Gly Leu Met Lys Gly Asn Lys Arg Glu Glu Gln Leu Gly
                20                  25                  30

Pro Glu Pro Ala Ala Pro Gln Gln Pro Thr Ala Glu Glu Ala Leu
                35                  40                  45

Ile Glu Phe His Arg Ser Tyr Arg Glu Leu Phe Glu Phe Phe Cys Asn
            50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

-continued

```
Met Met Tyr Trp Gln Phe Gly Leu Leu Phe Gly Glu Tyr Phe Ser Tyr
                100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
        130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His Pro Met Tyr Gly Asn
290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
    370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
        435                 440                 445

Lys His Ser Ser Trp Gly Tyr Cys Tyr Tyr Lys Leu Gln Val Asp Phe
    450                 455                 460

Ser Ser Asp His Leu Gly Cys Phe Thr Lys Cys Arg Lys Pro Cys Ser
465                 470                 475                 480

Val Thr Ser Tyr Gln Leu Ser Ala Gly Tyr Ser Arg Trp Pro Ser Val
                485                 490                 495

Thr Ser Gln Glu Trp Val Phe Gln Met Leu Ser Arg Gln Asn Asn Tyr
            500                 505                 510

Thr Val Asn Asn Lys Arg Asn Gly Val Ala Lys Val Asn Ile Phe Phe
```

```
                    515                 520                 525
Lys Glu Leu Asn Tyr Lys Thr Asn Ser Glu Ser Pro Ser Val Thr Met
    530                 535                 540

Val Thr Leu Leu Ser Asn Leu Gly Ser Gln Trp Ser Leu Trp Phe Gly
545                 550                 555                 560

Ser Ser Val Leu Ser Val Val Glu Met Ala Glu Leu Val Phe Asp Leu
                    565                 570                 575

Leu Val Ile Met Phe Leu Met Leu Leu Arg Arg Phe Arg Ser Arg Tyr
                580                 585                 590

Trp Ser Pro Gly Arg Gly Gly Arg Gly Ala Gln Glu Val Ala Ser Thr
            595                 600                 605

Leu Ala Ser Ser Pro Pro Ser His Phe Cys Pro His Pro Met Ser Leu
    610                 615                 620

Ser Leu Ser Gln Pro Gly Pro Ala Pro Ser Pro Ala Leu Thr Ala Pro
625                 630                 635                 640

Pro Pro Ala Tyr Ala Thr Leu Gly Pro Arg Pro Ser Pro Gly Gly Ser
                    645                 650                 655

Ala Gly Ala Ser Ser Ser Thr Cys Pro Leu Gly Gly Pro
                660                 665

<210> SEQ ID NO 15
<211> LENGTH: 728
<212> TYPE: PRT
<213> ORGANISM: Homo sapiens

<400> SEQUENCE: 15

Met Gly Met Ala Arg Gly Ser Leu Thr Arg Val Pro Gly Val Met Gly
1               5                   10                  15

Glu Gly Thr Gln Gly Pro Glu Leu Ser Leu Asp Pro Asp Pro Cys Ser
                20                  25                  30

Pro Gln Ser Thr Pro Gly Leu Met Lys Gly Asn Lys Leu Glu Glu Gln
            35                  40                  45

Asp Pro Arg Pro Leu Gln Pro Ile Pro Gly Leu Met Glu Gly Asn Lys
    50                  55                  60

Leu Glu Glu Gln Asp Ser Ser Pro Pro Gln Ser Thr Pro Gly Leu Met
65                  70                  75                  80

Lys Gly Asn Lys Arg Glu Glu Gln Gly Leu Gly Pro Glu Pro Ala Ala
                85                  90                  95

Pro Gln Gln Pro Thr Ala Glu Glu Ala Leu Ile Glu Phe His Arg
            100                 105                 110

Ser Tyr Arg Glu Leu Phe Glu Phe Cys Asn Asn Thr Thr Ile His
    115                 120                 125

Gly Ala Ile Arg Leu Val Cys Ser Gln His Asn Arg Met Lys Thr Ala
130                 135                 140

Phe Trp Ala Val Leu Trp Leu Cys Thr Phe Gly Met Met Tyr Trp Gln
145                 150                 155                 160

Phe Gly Leu Leu Phe Gly Glu Tyr Phe Ser Tyr Pro Val Ser Leu Asn
                165                 170                 175

Ile Asn Leu Asn Ser Asp Lys Leu Val Phe Pro Ala Val Thr Ile Cys
            180                 185                 190

Thr Leu Asn Pro Tyr Arg Tyr Pro Glu Ile Lys Glu Glu Leu Glu Glu
    195                 200                 205

Leu Asp Arg Ile Thr Glu Gln Thr Leu Phe Asp Leu Tyr Lys Tyr Ser
    210                 215                 220
```

```
Ser Phe Thr Thr Leu Val Ala Gly Ser Arg Ser Arg Arg Asp Leu Arg
225                 230                 235                 240

Gly Thr Leu Pro His Pro Leu Gln Arg Leu Arg Val Pro Pro Pro Pro
            245                 250                 255

His Gly Ala Arg Arg Ala Arg Ser Val Ala Ser Ser Leu Arg Asp Asn
        260                 265                 270

Asn Pro Gln Val Asp Trp Lys Asp Trp Lys Ile Gly Phe Gln Leu Cys
    275                 280                 285

Asn Gln Asn Lys Ser Asp Cys Phe Tyr Gln Thr Tyr Ser Ser Gly Val
290                 295                 300

Asp Ala Val Arg Glu Trp Tyr Arg Phe His Tyr Ile Asn Ile Leu Ser
305                 310                 315                 320

Arg Leu Pro Glu Thr Leu Pro Ser Leu Glu Glu Asp Thr Leu Gly Asn
            325                 330                 335

Phe Ile Phe Ala Cys Arg Phe Asn Gln Val Ser Cys Asn Gln Ala Asn
                340                 345                 350

Tyr Ser His Phe His His Pro Met Tyr Gly Asn Cys Tyr Thr Phe Asn
        355                 360                 365

Asp Lys Asn Asn Ser Asn Leu Trp Met Ser Ser Met Pro Gly Ile Asn
    370                 375                 380

Asn Gly Leu Ser Leu Met Leu Arg Ala Glu Gln Asn Asp Phe Ile Pro
385                 390                 395                 400

Leu Leu Ser Thr Val Thr Gly Ala Arg Val Met Val His Gly Gln Asp
            405                 410                 415

Glu Pro Ala Phe Met Asp Asp Gly Gly Phe Asn Leu Arg Pro Gly Val
                420                 425                 430

Glu Thr Ser Ile Ser Met Arg Lys Glu Thr Leu Asp Arg Leu Gly Gly
        435                 440                 445

Asp Tyr Gly Asp Cys Thr Lys Asn Gly Ser Asp Val Pro Val Glu Asn
    450                 455                 460

Leu Tyr Pro Ser Lys Tyr Thr Gln Gln Val Cys Ile His Ser Cys Phe
465                 470                 475                 480

Gln Glu Ser Met Ile Lys Glu Cys Gly Cys Ala Tyr Ile Phe Tyr Pro
            485                 490                 495

Arg Pro Gln Asn Val Glu Tyr Cys Asp Tyr Arg Lys His Ser Ser Trp
        500                 505                 510

Gly Tyr Cys Tyr Tyr Lys Leu Gln Val Asp Phe Ser Ser Asp His Leu
    515                 520                 525

Gly Cys Phe Thr Lys Cys Arg Lys Pro Cys Ser Val Thr Ser Tyr Gln
530                 535                 540

Leu Ser Ala Gly Tyr Ser Arg Trp Pro Ser Val Thr Ser Gln Glu Trp
545                 550                 555                 560

Val Phe Gln Met Leu Ser Arg Gln Asn Asn Tyr Thr Val Asn Asn Lys
            565                 570                 575

Arg Asn Gly Val Ala Lys Val Asn Ile Phe Lys Glu Leu Asn Tyr Tyr
                580                 585                 590

Lys Thr Asn Ser Glu Ser Pro Ser Val Thr Met Val Thr Leu Leu Ser
        595                 600                 605

Asn Leu Gly Ser Gln Trp Ser Leu Trp Phe Gly Ser Ser Val Leu Ser
    610                 615                 620

Val Val Glu Met Ala Glu Leu Val Phe Asp Leu Leu Val Ile Met Phe
625                 630                 635                 640

Leu Met Leu Leu Arg Arg Phe Arg Ser Arg Tyr Trp Ser Pro Gly Arg
```

```
                    645                 650                 655
Gly Gly Arg Gly Ala Gln Glu Val Ala Ser Thr Leu Ala Ser Ser Pro
            660                 665                 670

Pro Ser His Phe Cys Pro His Pro Met Ser Leu Ser Leu Ser Gln Pro
            675                 680                 685

Gly Pro Ala Pro Ser Pro Ala Leu Thr Ala Pro Pro Ala Tyr Ala
690                 695                 700

Thr Leu Gly Pro Arg Pro Ser Pro Gly Gly Ser Ala Gly Ala Ser Ser
705                 710                 715                 720

Ser Thr Cys Pro Leu Gly Gly Pro
            725

<210> SEQ ID NO 16
<211> LENGTH: 245
<212> TYPE: PRT
<213> ORGANISM: Homo sapiens

<400> SEQUENCE: 16

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
            35                  40                  45

Ile Glu Phe His Arg Ser Tyr Arg Glu Leu Phe Glu Phe Cys Asn
50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
            85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
            130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
            165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
            195                 200                 205

Ser Leu Arg Asp Asn Asn Pro Gln Val Asp Trp Lys Asp Trp Lys Ile
            210                 215                 220

Gly Phe Gln Leu Glu Leu Ser Leu Pro Pro Asp Val Trp Lys
225                 230                 235                 240

Leu Leu Tyr Phe Gly
            245

<210> SEQ ID NO 17
<211> LENGTH: 650
<212> TYPE: PRT
<213> ORGANISM: Homo sapiens
```

<400> SEQUENCE: 17

```
Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
        35                  40                  45

Ile Glu Phe His Arg Ser Tyr Arg Glu Leu Phe Glu Phe Phe Cys Asn
    50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
                85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
        115                 120                 125

Ala Val Thr Ile Cys Thr Leu Asn Pro Tyr Arg Tyr Pro Glu Ile Lys
    130                 135                 140

Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
    210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
            260                 265                 270

Asp Thr Leu Gly Asn Phe Ile Phe Ala Cys Arg Phe Asn Gln Val Ser
        275                 280                 285

Cys Asn Gln Ala Asn Tyr Ser His Phe His His Pro Met Tyr Gly Asn
    290                 295                 300

Cys Tyr Thr Phe Asn Asp Lys Asn Asn Ser Asn Leu Trp Met Ser Ser
305                 310                 315                 320

Met Pro Gly Ile Asn Asn Val Thr Gly Ala Arg Val Met Val His Gly
                325                 330                 335

Gln Asp Glu Pro Ala Phe Met Asp Asp Gly Gly Phe Asn Leu Arg Pro
            340                 345                 350

Gly Val Glu Thr Ser Ile Ser Met Arg Lys Glu Thr Leu Asp Arg Leu
        355                 360                 365

Gly Gly Asp Tyr Gly Asp Cys Thr Lys Asn Gly Ser Asp Val Pro Val
    370                 375                 380

Glu Asn Leu Tyr Pro Ser Lys Tyr Thr Gln Gln Val Cys Ile His Ser
385                 390                 395                 400

Cys Phe Gln Glu Ser Met Ile Lys Glu Cys Gly Cys Ala Tyr Ile Phe
                405                 410                 415
```

```
Tyr Pro Arg Pro Gln Asn Val Glu Tyr Cys Asp Tyr Arg Lys His Ser
            420                 425                 430

Ser Trp Gly Tyr Cys Tyr Tyr Lys Leu Gln Val Asp Phe Ser Ser Asp
            435                 440                 445

His Leu Gly Cys Phe Thr Lys Cys Arg Lys Pro Cys Ser Val Thr Ser
            450                 455                 460

Tyr Gln Leu Ser Ala Gly Tyr Ser Arg Trp Pro Ser Val Thr Ser Gln
465                 470                 475                 480

Glu Trp Val Phe Gln Met Leu Ser Arg Gln Asn Asn Tyr Thr Val Asn
            485                 490                 495

Asn Lys Arg Asn Gly Val Ala Lys Val Asn Ile Phe Phe Lys Glu Leu
            500                 505                 510

Asn Tyr Lys Thr Asn Ser Glu Ser Pro Ser Val Thr Met Val Thr Leu
            515                 520                 525

Leu Ser Asn Leu Gly Ser Gln Trp Ser Leu Trp Phe Gly Ser Ser Val
            530                 535                 540

Leu Ser Val Val Glu Met Ala Glu Leu Val Phe Asp Leu Leu Val Ile
545                 550                 555                 560

Met Phe Leu Met Leu Leu Arg Arg Phe Arg Ser Arg Tyr Trp Ser Pro
            565                 570                 575

Gly Arg Gly Gly Arg Gly Ala Gln Glu Val Ala Ser Thr Leu Ala Ser
            580                 585                 590

Ser Pro Pro Ser His Phe Cys Pro His Pro Met Ser Leu Ser Leu Ser
            595                 600                 605

Gln Pro Gly Pro Ala Pro Ser Pro Ala Leu Thr Ala Pro Pro Ala
            610                 615                 620

Tyr Ala Thr Leu Gly Pro Arg Pro Ser Pro Gly Gly Ser Ala Gly Ala
625                 630                 635                 640

Ser Ser Ser Thr Cys Pro Leu Gly Gly Pro
                645                 650

<210> SEQ ID NO 18
<211> LENGTH: 691
<212> TYPE: PRT
<213> ORGANISM: Homo sapiens

<400> SEQUENCE: 18

Met Glu Gly Asn Lys Leu Glu Glu Gln Asp Ser Ser Pro Pro Gln Ser
1               5                   10                  15

Thr Pro Gly Leu Met Lys Gly Asn Lys Arg Glu Glu Gln Gly Leu Gly
            20                  25                  30

Pro Glu Pro Ala Ala Pro Gln Gln Pro Thr Ala Glu Glu Ala Leu
            35                  40                  45

Ile Glu Phe His Arg Ser Tyr Arg Glu Leu Phe Glu Phe Phe Cys Asn
50                  55                  60

Asn Thr Thr Ile His Gly Ala Ile Arg Leu Val Cys Ser Gln His Asn
65                  70                  75                  80

Arg Met Lys Thr Ala Phe Trp Ala Val Leu Trp Leu Cys Thr Phe Gly
            85                  90                  95

Met Met Tyr Trp Gln Phe Gly Leu Leu Phe Gly Glu Tyr Phe Ser Tyr
            100                 105                 110

Pro Val Ser Leu Asn Ile Asn Leu Asn Ser Asp Lys Leu Val Phe Pro
            115                 120                 125

Ala Val Thr Ile Cys Thr Leu Asn Pro Tyr Arg Tyr Pro Glu Ile Lys
```

-continued

```
            130                 135                 140
Glu Glu Leu Glu Glu Leu Asp Arg Ile Thr Glu Gln Thr Leu Phe Asp
145                 150                 155                 160

Leu Tyr Lys Tyr Ser Ser Phe Thr Thr Leu Val Ala Gly Ser Arg Ser
                165                 170                 175

Arg Arg Asp Leu Arg Gly Thr Leu Pro His Pro Leu Gln Arg Leu Arg
            180                 185                 190

Val Pro Pro Pro His Gly Ala Arg Arg Ala Arg Ser Val Ala Ser
        195                 200                 205

Ser Leu Arg Asp Asn Asn Pro Gln Val Asp Trp Lys Asp Trp Lys Ile
210                 215                 220

Gly Phe Gln Leu Cys Asn Gln Asn Lys Ser Asp Cys Phe Tyr Gln Thr
225                 230                 235                 240

Tyr Ser Ser Gly Val Asp Ala Val Arg Glu Trp Tyr Arg Phe His Tyr
                245                 250                 255

Ile Asn Ile Leu Ser Arg Leu Pro Glu Thr Leu Pro Ser Leu Glu Glu
                260                 265                 270

Asp Thr Leu Gly Asn Phe Ile Phe Ala Cys Arg Phe Asn Gln Val Ser
            275                 280                 285

Cys Asn Gln Ala Asn Tyr Ser His Phe His His Pro Met Tyr Gly Asn
290                 295                 300

Cys Tyr Thr Phe Asn Asp Lys Asn Asn Ser Asn Leu Trp Met Ser Ser
305                 310                 315                 320

Met Pro Gly Ile Asn Asn Gly Leu Ser Leu Met Leu Arg Ala Glu Gln
                325                 330                 335

Asn Asp Phe Ile Pro Leu Leu Ser Thr Val Thr Gly Ala Arg Val Met
            340                 345                 350

Val His Gly Gln Asp Glu Pro Ala Phe Met Asp Asp Gly Gly Phe Asn
        355                 360                 365

Leu Arg Pro Gly Val Glu Thr Ser Ile Ser Met Arg Lys Glu Thr Leu
    370                 375                 380

Asp Arg Leu Gly Gly Asp Tyr Gly Asp Cys Thr Lys Asn Gly Ser Asp
385                 390                 395                 400

Val Pro Val Glu Asn Leu Tyr Pro Ser Lys Tyr Thr Gln Gln Val Cys
                405                 410                 415

Ile His Ser Cys Phe Gln Glu Ser Met Ile Lys Glu Cys Gly Cys Ala
            420                 425                 430

Tyr Ile Phe Tyr Pro Arg Pro Gln Asn Val Glu Tyr Cys Asp Tyr Arg
            435                 440                 445

Lys His Ser Ser Trp Gly Gln Val Arg Ser Leu Thr Pro Val Ile Pro
    450                 455                 460

Ala Leu Trp Glu Ala Glu Ala Gly Gly Ser Arg Gly Tyr Cys Tyr Tyr
465                 470                 475                 480

Lys Leu Gln Val Asp Phe Ser Ser Asp His Leu Gly Cys Phe Thr Lys
                485                 490                 495

Cys Arg Lys Pro Cys Ser Val Thr Ser Tyr Gln Leu Ser Ala Gly Tyr
            500                 505                 510

Ser Arg Trp Pro Ser Val Thr Ser Gln Glu Trp Val Phe Gln Met Leu
    515                 520                 525

Ser Arg Gln Asn Asn Tyr Thr Val Asn Asn Lys Arg Asn Gly Val Ala
530                 535                 540

Lys Val Asn Ile Phe Phe Lys Glu Leu Asn Tyr Lys Thr Asn Ser Glu
545                 550                 555                 560
```

```
Ser Pro Ser Val Thr Met Val Thr Leu Leu Ser Asn Leu Gly Ser Gln
            565                 570                 575

Trp Ser Leu Trp Phe Gly Ser Ser Val Leu Ser Val Val Glu Met Ala
            580                 585                 590

Glu Leu Val Phe Asp Leu Leu Val Ile Met Phe Leu Met Leu Leu Arg
            595                 600                 605

Arg Phe Arg Ser Arg Tyr Trp Ser Pro Gly Arg Gly Arg Gly Arg Ala
            610                 615                 620

Gln Glu Val Ala Ser Thr Leu Ala Ser Ser Pro Pro Ser His Phe Cys
625                 630                 635                 640

Pro His Pro Met Ser Leu Ser Leu Ser Gln Pro Gly Pro Ala Pro Ser
            645                 650                 655

Pro Ala Leu Thr Ala Pro Pro Ala Tyr Ala Thr Leu Gly Pro Arg
            660                 665                 670

Pro Ser Pro Gly Gly Ser Ala Gly Ala Ser Ser Thr Cys Pro Leu
            675                 680                 685

Gly Gly Pro
    690

<210> SEQ ID NO 19
<211> LENGTH: 692
<212> TYPE: PRT
<213> ORGANISM: Homo sapiens

<400> SEQUENCE: 19

Met Ser Ser Ile Lys Gly Asn Lys Leu Glu Glu Gln Asp Pro Arg Pro
1               5                   10                  15

Leu Gln Pro Ile Pro Gly Leu Met Glu Gly Asn Lys Leu Glu Glu Gln
            20                  25                  30

Asp Ser Ser Pro Pro Gln Ser Thr Pro Gly Leu Met Lys Gly Asn Lys
            35                  40                  45

Arg Glu Glu Gln Gly Leu Gly Pro Glu Pro Ala Ala Pro Gln Gln Pro
    50                  55                  60

Thr Ala Glu Glu Glu Ala Leu Ile Glu Phe His Arg Ser Tyr Arg Glu
65                  70                  75                  80

Leu Phe Glu Phe Phe Cys Asn Asn Thr Thr Ile His Gly Ala Ile Arg
                85                  90                  95

Leu Val Cys Ser Gln His Asn Arg Met Lys Thr Ala Phe Trp Ala Val
            100                 105                 110

Leu Trp Leu Cys Thr Phe Gly Met Met Tyr Trp Gln Phe Gly Leu Leu
            115                 120                 125

Phe Gly Glu Tyr Phe Ser Tyr Pro Val Ser Leu Asn Ile Asn Leu Asn
    130                 135                 140

Ser Asp Lys Leu Val Phe Pro Ala Val Thr Ile Cys Thr Leu Asn Pro
145                 150                 155                 160

Tyr Arg Tyr Pro Glu Ile Lys Glu Glu Leu Glu Glu Leu Asp Arg Ile
                165                 170                 175

Thr Glu Gln Thr Leu Phe Asp Leu Tyr Lys Tyr Ser Ser Phe Thr Thr
            180                 185                 190

Leu Val Ala Gly Ser Arg Ser Arg Arg Asp Leu Arg Gly Thr Leu Pro
            195                 200                 205

His Pro Leu Gln Arg Leu Arg Val Pro Pro Pro His Gly Ala Arg
    210                 215                 220

Arg Ala Arg Ser Val Ala Ser Ser Leu Arg Asp Asn Asn Pro Gln Val
```

-continued

```
                225                 230                 235                 240
Asp Trp Lys Asp Trp Lys Ile Gly Phe Gln Leu Cys Asn Gln Asn Lys
                    245                 250                 255
Ser Asp Cys Phe Tyr Gln Thr Tyr Ser Ser Gly Val Asp Ala Val Arg
                260                 265                 270
Glu Trp Tyr Arg Phe His Tyr Ile Asn Ile Leu Ser Arg Leu Pro Glu
            275                 280                 285
Thr Leu Pro Ser Leu Glu Glu Asp Thr Leu Gly Asn Phe Ile Phe Ala
        290                 295                 300
Cys Arg Phe Asn Gln Val Ser Cys Asn Gln Ala Asn Tyr Ser His Phe
305                 310                 315                 320
His His Pro Met Tyr Gly Asn Cys Tyr Thr Phe Asn Asp Lys Asn Asn
                    325                 330                 335
Ser Asn Leu Trp Met Ser Ser Met Pro Gly Ile Asn Asn Gly Leu Ser
                340                 345                 350
Leu Met Leu Arg Ala Glu Gln Asn Asp Phe Ile Pro Leu Leu Ser Thr
            355                 360                 365
Val Thr Gly Ala Arg Val Met Val His Gly Gln Asp Glu Pro Ala Phe
        370                 375                 380
Met Asp Asp Gly Gly Phe Asn Leu Arg Pro Gly Val Glu Thr Ser Ile
385                 390                 395                 400
Ser Met Arg Lys Glu Thr Leu Asp Arg Leu Gly Gly Asp Tyr Gly Asp
                    405                 410                 415
Cys Thr Lys Asn Gly Ser Asp Val Pro Val Glu Asn Leu Tyr Pro Ser
                420                 425                 430
Lys Tyr Thr Gln Gln Val Cys Ile His Ser Cys Phe Gln Glu Ser Met
            435                 440                 445
Ile Lys Glu Cys Gly Cys Ala Tyr Ile Phe Tyr Pro Arg Pro Gln Asn
        450                 455                 460
Val Glu Tyr Cys Asp Tyr Arg Lys His Ser Ser Trp Gly Tyr Cys Tyr
465                 470                 475                 480
Tyr Lys Leu Gln Val Asp Phe Ser Ser Asp His Leu Gly Cys Phe Thr
                    485                 490                 495
Lys Cys Arg Lys Pro Cys Ser Val Thr Ser Tyr Gln Leu Ser Ala Gly
                500                 505                 510
Tyr Ser Arg Trp Pro Ser Val Thr Ser Gln Glu Trp Val Phe Gln Met
            515                 520                 525
Leu Ser Arg Gln Asn Asn Tyr Thr Val Asn Asn Lys Arg Asn Gly Val
        530                 535                 540
Ala Lys Val Asn Ile Phe Phe Lys Glu Leu Asn Tyr Lys Thr Asn Ser
545                 550                 555                 560
Glu Ser Pro Ser Val Thr Met Val Thr Leu Leu Ser Asn Leu Gly Ser
                    565                 570                 575
Gln Trp Ser Leu Trp Phe Gly Ser Ser Val Leu Ser Val Glu Met
                580                 585                 590
Ala Glu Leu Val Phe Asp Leu Leu Val Ile Met Phe Leu Met Leu Leu
            595                 600                 605
Arg Arg Phe Arg Ser Arg Tyr Trp Ser Pro Gly Arg Gly Gly Arg Gly
        610                 615                 620
Ala Gln Glu Val Ala Ser Thr Leu Ala Ser Ser Pro Ser His Phe
625                 630                 635                 640
Cys Pro His Pro Met Ser Leu Ser Leu Ser Gln Pro Gly Pro Ala Pro
                    645                 650                 655
```

```
Ser Pro Ala Leu Thr Ala Pro Pro Ala Tyr Ala Thr Leu Gly Pro
            660             665             670

Arg Pro Ser Pro Gly Gly Ser Ala Gly Ala Ser Ser Ser Thr Cys Pro
            675             680             685

Leu Gly Gly Pro
    690
```